US012797356B2

(12) United States Patent
Qiu et al.

(10) Patent No.: US 12,797,356 B2
(45) Date of Patent: Nov. 17, 2026

(54) PHARMACEUTICAL COMPOSITION COMPRISING CABAZITAXEL PRODRUG-CYCLODEXTRIN INCLUSION COMPLEX, AND APPLICATIONS THEREOF

(71) Applicant: Salus Therapeutics Inc., Taipei City (TW)

(72) Inventors: Yong Qiu, San Diego, CA (US); Yu-Cheng Tseng, Taipei City (TW); Yu-Yang Chiang, New Taipei City (TW)

(73) Assignee: SALUS THERAPEUTICS INC., Taipei City (TW)

( * ) Notice: Subject to any disclaimer, the term of this patent is extended or adjusted under 35 U.S.C. 154(b) by 280 days.

(21) Appl. No.: 18/755,748

(22) Filed: Jun. 27, 2024

(65) Prior Publication Data

US 2025/0017891 A1 Jan. 16, 2025

Related U.S. Application Data

(60) Provisional application No. 63/524,863, filed on Jul. 4, 2023.

(51) Int. Cl.

*A61K 31/33* (2006.01)
*A61K 31/337* (2006.01)
*A61K 47/69* (2017.01)

(52) U.S. Cl.

CPC ........ *A61K 31/337* (2013.01); *A61K 47/6951* (2017.08)

(58) Field of Classification Search

CPC .................................................... A61K 31/337

See application file for complete search history.

(56) References Cited

U.S. PATENT DOCUMENTS 8,927,592 B2 1/2015 Gupta
2013/0196946 A1* 8/2013 Wolfgang ........... C08B 37/0015 514/58

OTHER PUBLICATIONS

Sun et al., "Current development of cabazitaxel drug delivery systems". Wires Nanomed Nanobiotechnol. 2022: e1854, published on Sep. 25, 2022.

Boyapelly et al., "Synthesis and characterization of a phosphate prodrug of isoliquiritigenin". J. Nat. Prod. 2017, 80, pp. 879-886, published on Mar. 2, 2017.

Davis and Brewster, "Cyclodextrin-based pharmaceutics: past, present and future". Nature Reviews Frug Discovery. 2004, vol. 3, pp. 1023-1035, published on Dec. 1, 2004.

* cited by examiner

*Primary Examiner* — Shawquia Jackson
(74) *Attorney, Agent, or Firm* — WPAT, PC

(57) ABSTRACT

Provided is a pharmaceutical composition comprising: (a) a cabazitaxel prodrug represented by Formula 1 or a pharmaceutical acceptable salt thereof, and (b) a cyclodextrin (Formula 1)

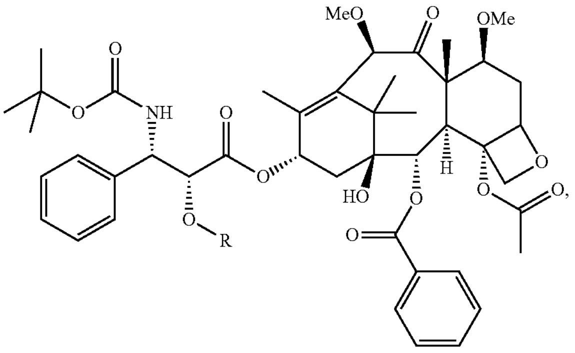

wherein R—O— is an ester group. Also provided is a method of treating a tumor in a subject in need thereof, comprising administering to the subject a therapeutically effective amount of the pharmaceutical composition.

11 Claims, 12 Drawing Sheets

PHARMACEUTICAL COMPOSITION COMPRISING CABAZITAXEL PRODRUG-CYCLODEXTRIN INCLUSION COMPLEX, AND APPLICATIONS THEREOF

CROSS-REFERENCE TO RELATED APPLICATION

Pursuant to 35 U.S.C. § 119(e), this application claims the benefit of the priority to U.S. Provisional Patent Application No. 63/524,863, filed on Jul. 4, 2023. The content of the prior application is incorporated herein by its entirety.

BACKGROUND OF THE INVENTION

1. Field of the Invention

The present invention relates to a pharmaceutical composition comprising a cabazitaxel prodrug-cyclodextrin inclusion complex. The invention also provides a method of treating a tumor using the pharmaceutical composition.

2. Description of the Prior Arts

Cabazitaxel is a second-generation antineoplastic agent of the taxoid family, and it is developed after the first-generation antineoplastic agent of taxanes, notably paclitaxel and docetaxel, which are well-established used in the treatments for a broad range of common solid tumors. Cabazitaxel has been shown to have activities in both docetaxel-sensitive and docetaxel-resistant tumors, possibly because of the lower P-glycoprotein (P-gp) affinity relative to that of paclitaxel and docetaxel.

The current commercial product of cabazitaxel is Jevtana®, marketed by Sanofi-Aventis. Jevtana® was approved by the US FDA in 2010 based on a Phase III study showing longer overall survival compared to mitoxantrone treatment in metastatic, castration-resistant prostate cancer patients previously treated with docetaxel. However, cabazitaxel is almost insoluble even in the mixed solvent of water and organic reagent. To overcome the low solubility problem, Jevtana® is formulated in 100% polysorbate 80 (Tween 80) and requires two-step dilution before administration. The Jevtana® kit consists of 2 vials, with one vial containing 60 mg cabazitaxel in 1.5 mL Tween 80, and another diluent vial containing 13% (w/w) ethanol in water for injection. In the $1^{st}$-step dilution, each vial of Jevtana® (cabazitaxel) with a concentration of 60 mg/1.5 mL must be mixed with the entire contents of the supplied diluent, leading to the resultant solution containing 10 mg/mL of cabazitaxel. The initial diluted cabazitaxel solution (10 mg/mL) requires further dilution before administration, which should be done immediately (i.e., within 30 minutes). The $2^{nd}$-step dilution is done by withdrawing the recommended dose from the 10 mg/mL cabazitaxel solution prepared from the $1^{st}$-step dilution using a calibrated syringe, and further diluting the 10 mg/mL cabazitaxel solution in a sterile 250 mL PVC-free container full of either 0.9% sodium chloride solution or 5% dextrose solution into an infusion solution. As the final infusion solution is supersaturated, it may crystallize over time. So the resulting infusion solution (in either 0.9% sodium chloride solution or 5% dextrose solution) should be used within 8 hours at ambient temperature (including the one-hour infusion) or within a total of 24 hours if refrigerated (including the one-hour infusion).

Polysorbate 80 used in the current commercial (Jevtana®) product has been implicated in numerous systemic and injection- and infusion-site adverse events (ISAEs). In the Jevtana® product label, the warning includes contradictions of history of severe hypersensitivity to Jevtana® or polysorbate 80. Severe hypersensitivity reactions characterized by generalized rash/erythema, hypotension, and bronchospasm can occur, and require immediate discontinuation of the Jevtana® infusion and administration of an appropriate therapy. To reduce the risk and/or severity of hypersensitivity, premedication at least 30 minutes before each dose of Jevtana® is recommended using antihistamine (dexchlorpheniramine 5 mg, or diphenhydramine 25 mg or equivalent antihistamine), corticosteroid (dexamethasone 8 mg or equivalent steroid), and H2 antagonist (ranitidine 50 mg or equivalent H2 antagonist).

Ethanol is also used in the diluent of the current commercial product. In a drug safety communication, a Safety Announcement was issued by the FDA in June 2014, warning the intravenous chemotherapy drug docetaxel containing ethanol may cause patients to experience intoxication or feel drunk during and after treatment. The warning was issued based on a review of the FDA Adverse Event Reporting System database and medical literature that revealed three cases of alcohol intoxication associated with docetaxel. Although the ethanol content in the current commercial product of cabazitaxel (Jevtana®) is much lower than the ethanol content of the docetaxel product, it still presents a potential intoxication risk for patients with hypersensitivity.

Therefore, there is a need for a cabazitaxel composition that has improved solubility and reduced hypersensitivity and toxicity.

SUMMARY OF THE INVENTION

To overcome the shortcomings, the present invention provides a pharmaceutical composition comprising a cabazitaxel prodrug-cyclodextrin inclusion complex, which has an improved aqueous solubility and long-term storage stability. The pharmaceutical composition of the present invention comprises no polysorbate 80 (surfactant, which may result in diarrhea and hypersensitivity reactions in patients) or alcohol (which may result in intoxication), and allows administration of cabazitaxel to patients without the need of premedication. In addition, the pharmaceutical composition of the present invention may be administered via an oral route.

In one aspect, the present invention provides a pharmaceutical composition comprising a cabazitaxel prodrug-cyclodextrin inclusion complex, which comprises: (a) a cabazitaxel prodrug represented by Formula 1 or a pharmaceutical acceptable salt thereof, and (b) a cyclodextrin (Formula 1)

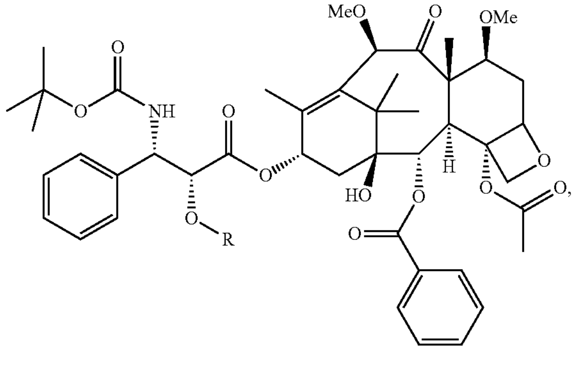

wherein,

R—O— is a phosphate ester group ($O{=}P(OH)_2$—O—), a phosphate alkyloxy ester group ($R^1$—O—P(=O)(OH)—O—), a methyl dihydrogen phosphate ester group ($O{=}P(OCH_3)(OH)$—O—), a sulfate ester group ($SO_3^-$—O—), a methyl hydrogen sulfate ester group ($SO_2(CH_3O)$—O—), an ethyl hydrogen sulfate ester group ($SO_2(CH_3CH_2O)$—O—), a carboxylic ester group ($R^1$—C(=O)—O—), an aromatic carboxylic ester group ($R^1$—$C_6H_5$—C(=O)—O—), a carbonate ester group ($R^1$—O—C(=O)—O—), an aromatic carbonate ester group ($R^1$—$C_6H_5$—O—C(=O)—O—), a benzoic acid ester group ($C_6H_5C$(=O)—O—), a nitrobenzoic acid ester group (($NO_2$)—$C_6H_4C$(=O)—O—), a carbamate ester group ($R^1$—HN—C(=O)—O—), or an amino acid ester group; and $R^1$ is an optionally substituted straight or branched alkyl chain, alkenyl chain, or alkynyl chain; an optionally substituted straight or branched carboxylic acid group, alkyl carboxylic acid group, alkenyl carboxylic acid group, or alkynyl carboxylic acid group; or an optionally substituted straight or branched alkyl carboxylic acid amide group of an amino acid, alkenyl carboxylic acid amide of an amino acid, alkynyl carboxylic acid amide of an amino acid; each of which having a total number of 1 to 30 carbons.

In another aspect, the present invention provides a method of treating a tumor in a subject in need thereof, comprising administering to the subject a therapeutically effective amount of the above-mentioned pharmaceutical composition.

The term "prodrug" used herein indicates a therapeutic agent precursor that may be intrinsically largely inactive, but is transformed within the host (such as, the subject in need) into one or more active metabolites that exhibit therapeutic efficacy. The administration of a prodrug of the present invention to a subject in need produces a desired rate of the conversion to the parent drug cabazitaxel when the prodrug reaches its intended destination.

The term "inclusion complex" herein indicates a cyclodextrin inclusion complex which can be formed through complexation of a drug (or a prodrug) and a cyclodextrin. The inclusion complex may be prepared in a solution, in a semisolid state, or in a solid state. When the inclusion complex is prepared in a solution, for example, the inclusion complex may be obtained by dissolving a drug and a cyclodextrin in water, an organic solvent or a combination thereof, or in a supercritical fluid; and isolating the resulting inclusion complex by crystallization or drying. When the inclusion complex is prepared in a semisolid state, for example, the inclusion complex may be obtained by mixing a drug and a cyclodextrin with a small amount of water, an alcohol or a combination thereof, and kneading the resulting mixture homogeneously until dried. When the inclusion complex is prepared in a solid state, for example, the inclusion complex may be obtained by mixing a drug and a cyclodextrin and heating at a temperature lower than the fusion point of the compounds in a sealed container; or, the inclusion complex may be obtained by mechanochemical activation, specifically, the inclusion complex is obtained by mixing a drug and a cyclodextrin and grinding the resulting mixture to obtain the final product. The above grinding may be carried out by mixing a drug, a cyclodextrin and milling beads, and grinding the resulting mixture by a homogenizer. The milling beads may be any beads suitable for a homogenizer. The material of the milling beads includes, but is not limited to, stainless steel, glass, plastic, siloxane, and the like. The size of the milling beads may be 0.07 millimeter (mm) to 50 mm, 0.1 mm to 45 mm, 0.1 mm to 40 mm, 0.1 mm to 35 mm, 0.1 mm to 30 mm, 0.1 mm to 25 mm, 0.1 mm to 20 mm, 0.1 mm to 15 mm, 0.1 mm to 10 mm, 0.4 mm to 6 mm, or 1 mm to 3 mm, but is not limited thereto.

In some embodiments of the present invention, the amino acid is selected from natural amino acids or non-natural amino acids. In some embodiments of the present invention, the natural amino acids may be selected from alanine (Ala), arginine (Arg), asparagine (Asn), aspartate (Asp), cysteine (Cys), glutamine (Gln), glutamate (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), valine (Val), selenocysteine (Sec) and pyrrolysine (Pyl). The amino acid ester group may be formed with the carboxyl group next to the a carbon of the amino acid, or with the carboxyl group on the side chain of Asp or Glu.

In some embodiments of the present invention, $R^1$ is optionally substituted with one or more groups independently selected from halogen, optionally substituted C1-C6 alkyl, optionally substituted C1-C6 heteroalkyl with 1 or 2 heteroatoms independently selected from oxygen and nitrogen, optionally substituted C2-C6 alkenyl, optionally substituted C2-C6 alkynyl, optionally substituted C3-C6 cycloalkyl, optionally substituted C6-C14 aryl, optionally substituted 5-membered to 8-membered heterocycloalkyl, optionally substituted 5-membered to 10-membered heteroaryl, single α-amino acids and short peptides selected from peptide composed of 2, 3 or 4 α-amino acids, wherein the α-amino acids are independently selected from alanine, isoleucine, leucine, methionine, valine, phenylalanine, tryptophan, tyrosine, asparagine, cysteine, glutamine, serine, threonine, aspartic acid, glutamic acid, arginine, histidine, lysine, glycine, and proline. In some embodiments of the present invention, the halogen is selected from fluorine (F), chlorine (Cl), bromine (Br) and iodine (I).

In some embodiments of the present invention, $R^1$ is an optionally substituted straight or branched alkyl chain, and the alkyl chain may be a C1-C30 alkyl chain, preferably a C2-C24 alkyl chain, and more preferably a C3-C20 alkyl chain.

In some embodiments of the present invention, $R^1$ is an optionally substituted straight or branched alkenyl chain, and the alkenyl chain may be a C1-C30 alkenyl chain, preferably a C2-C24 alkenyl chain, and more preferably a C3-C20 alkenyl chain.

In some embodiments of the present invention, $R^1$ is an optionally substituted straight or branched alkynyl chain, and the alkynyl chain may be a C1-C30 alkynyl chain, preferably a C2-C24 alkynyl chain, and more preferably a C3-C20 alkynyl chain.

In some embodiments of the present invention, $R^1$ is an optionally substituted straight or branched carboxylic acid group, and the carboxylic acid group may be a C1 carboxylic acid group. In some embodiments of the present invention, $R^1$ is a carboxylic acid group, preferably formic acid group.

In some embodiments of the present invention, $R^1$ is an optionally substituted straight or branched alkyl carboxylic acid group, and the alkyl carboxylic acid group may be a C2-C30 alkyl carboxylic acid group, preferably a C3-C24 alkyl carboxylic acid group, and more preferably a C4-C20 alkyl carboxylic acid group. In some embodiments of the present invention, $R^1$ is a non-substituted straight alkyl carboxylic acid group having a total number of 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbons.

In some embodiments of the present invention, $R^1$ is an optionally substituted straight or branched alkenyl carboxylic acid group, and the alkenyl carboxylic acid group may be a C2-C30 alkenyl carboxylic acid group, preferably a C3-C24 alkenyl carboxylic acid group, and more preferably a C4-9 C20 alkenyl carboxylic acid group. In some embodiments of the present invention, $R^1$ is a non-substituted straight or branched alkenyl carboxylic acid group having a total number of 2, 3, 4, 5, 6, 7, 8, 9, 10, 11 or 12 carbons.

In some embodiments of the present invention, $R^1$ is an optionally substituted straight or branched alkynyl carboxylic acid group, and the alkynyl carboxylic acid group may be a C2-C30 alkynyl carboxylic acid group, preferably a C3-C24 alkynyl carboxylic acid group, and more preferably a C4-C20 alkynyl carboxylic acid group. In some embodiments of the present invention, $R^1$ is a non-substituted straight alkynyl carboxylic acid group having a total number of 2, 3 or 4 carbons.

In some embodiments of the present invention, $R^1$ is an optionally substituted straight or branched alkyl carboxylic acid amide group of an amino acid, and the alkyl carboxylic acid amide group of an amino acid may be a C1-C30 alkyl carboxylic acid amide group of an amino acid, preferably a C2-C24 alkyl carboxylic acid amide group of an amino acid, and more preferably a C3-C20 alkyl carboxylic acid amide group of an amino acid.

In some embodiments of the present invention, $R^1$ is an optionally substituted straight or branched alkenyl carboxylic acid amide group of an amino acid, and the alkenyl carboxylic acid amide group of an amino acid may be a C1-C30 alkenyl carboxylic acid amide group of an amino acid, preferably a C2-C24 alkenyl carboxylic acid amide group of an amino acid, and more preferably a C3-C20 alkenyl carboxylic acid amide group of an amino acid.

In some embodiments of the present invention, $R^1$ is an optionally substituted straight or branched alkynyl carboxylic acid amide group of an amino acid, the alkynyl carboxylic acid amide group of an amino acid may be a C1-C30 alkynyl carboxylic acid amide group of an amino acid, preferably a C2-C24 alkynyl carboxylic acid amide group of an amino acid, and more preferably a C3-C20 alkynyl carboxylic acid amide group of an amino acid.

In some embodiments of the present invention, R—O— is a carboxylic ester group ($R^1$—C(═O)—O—) and $R^1$ is an optionally substituted straight or branched carboxylic acid group, alkyl carboxylic acid group, alkenyl carboxylic acid group, or alkynyl carboxylic acid group.

In some embodiments of the present invention, R—O— is a carboxylic ester group ($R^1$—C(═O)—O—) and $R^1$ is a non-substituted straight carboxylic acid group. In some embodiments of the present invention, the cabazitaxel prodrug is cabazitaxel oxalate.

In some embodiments of the present invention, R—O— is a carboxylic ester group ($R^1$—C(═O)—O—) and $R^1$ is a non-substituted straight alkyl carboxylic acid group. In some embodiments of the present invention, the cabazitaxel prodrug is cabazitaxel malonate, cabazitaxel succinate, cabazitaxel glutarate, cabazitaxel adipate, cabazitaxel pimelicate, cabazitaxel subericate, cabazitaxel azelaicate, cabazitaxel sebacicate, cabazitaxel undecanedioic acid ester, cabazitaxel dodecanedioic acid ester, cabazitaxel tridecanedioic acid ester, cabazitaxel hexadecanedioic acid ester, cabazitaxel heneicosanedioic acid ester, cabazitaxel docosanedioic acid ester, or cabazitaxel triacontanedioic acid ester.

In some embodiments of the present invention, R—O— is a carboxylic ester group ($R^1$—C(═O)—O—) and $R^1$ is a non-substituted straight or branched alkenyl carboxylic acid group. In some embodiments of the present invention, the cabazitaxel prodrug is cabazitaxel maleicate, cabazitaxel fumarate, cabazitaxel glutaconate, cabazitaxel (e)-pent-2-enedioic acid ester, cabazitaxel 2-decenedioic acid ester, cabazitaxel traumatate, cabazitaxel muconate, cabazitaxel glutinate, cabazitaxel citraconate, cabazitaxel mesaconate, or cabazitaxel itaconate.

In some embodiments of the present invention, R—O— is a carboxylic ester group ($R^1$—C(═O)—O—) and $R^1$ is a non-substituted straight alkynyl carboxylic acid group. In some embodiments of the present invention, the cabazitaxel prodrug is cabazitaxel acetylenedicarboxylate.

In some embodiments of the present invention, the cabazitaxel prodrug is cabazitaxel phosphate.

In some embodiments of the present invention, R—O— is a benzoic acid ester group ($C_6H_5C$(═O)—O—) or a nitrobenzoic acid ester group (($NO_2$)—$C_6H_4C$(═O)—O—). In some embodiments of the present invention, the nitrobenzoic acid ester group (($NO_2$)—$C_6H_4C$(═O)—O—) comprises ortho-nitrobenzoic ester group, meta-nitrobenzoic acid ester group, and para-nitrobenzoic acid ester group.

In some embodiments of the present invention, the cabazitaxel prodrug is cabazitaxel benzoate or cabazitaxel nitrobenzoate. In some embodiments of the present invention, the nitrobenzoate comprises ortho-nitrobenzoate, meta-nitrobenzoate and para-nitrobenzoate The term "cyclodextrin" indicates cyclodextrins (also referred to as "CD" hereinafter) having utility for solubilizing and stabilizing active substance(s) (such as the cabazitaxel prodrug represented by Formula 1 of the present invention). The relative amount of active substance(s) in compositions can be adjusted by cyclodextrin(s). In the present invention, cyclodextrin can be either used alone or in a mixture of two or more cyclodextrins.

In some embodiments of the present invention, the cyclodextrin is selected from α-cyclodextrin, β-cyclodextrin, γ-cyclodextrin, or a combination thereof.

The α-cyclodextrin can be, for example, a naturally occurring α-cyclodextrin, a synthetic α-cyclodextrin, or a combination thereof.

The β-cyclodextrin can be, for example, a naturally occurring β-cyclodextrin, a sulfobutyl ether beta cyclodextrin (SBECD), 2-hydroxypropyl-β-cyclodextrin (HPBCD), a randomly methylated-β-cyclodextrin, or a combination thereof.

The γ-cyclodextrin can be, for example, a naturally occurring γ-cyclodextrin, 2-hydroxypropyl-γ-cyclodextrin (HPγCD), or a combination thereof.

In some embodiments of the present invention, said cabazitaxel prodrug and cyclodextrin are in a molar ratio of cabazitaxel prodrug to cyclodextrin from about 1:30 to about 1:0.5, or from about 1:30 to about 1:1, or from about 1:30 to about 1:1.5, or from about 1:30 to about 1:2, or from about 1:30 to about 1:2.5. In some embodiments of the present invention, said cabazitaxel prodrug and cyclodextrin are in a molar ratio of cabazitaxel prodrug to cyclodextrin from about 1:25 to about 1:0.1, or from about 1:20 to about 1:0.1, or from about 1:15 to about 1:0.1, or from about 1:10 to about 1:0.1, or from about 1:5 to about 1:0.1. In some embodiments of the present invention, said cabazitaxel prodrug and cyclodextrin are in a molar ratio of cabazitaxel prodrug to cyclodextrin from about 1:30 to about 1:0.5, or from about 1:30 to about 1:1, or from about 1:30 to about 1:2.

In some embodiments of the present invention, the cyclodextrin is 3-cyclodextrin and said cabazitaxel prodrug and β-cyclodextrin are in a molar ratio of cabazitaxel prodrug to β-cyclodextrin from about 1:30 to about 1:0.5.

In some embodiments of the present invention, the cyclodextrin in the composition is SBECD and said cabazitaxel prodrug and SBECD are in a molar ratio of cabazitaxel prodrug to SBECD from about 1:30 to about 1:0.5.

In some embodiments of the present invention, the cyclodextrin of the composition is HPBCD and said cabazitaxel prodrug and HPBCD are in a molar ratio of cabazitaxel prodrug to HPBCD from about 1:30 to about 1:0.5.

In some embodiments of the present invention, the cyclodextrin is a mixture of SBECD and HPBCD at a ratio of 10:1 to 1:10, and is at the molar ratio of cabazitaxel prodrug to the SBECD/HPBCD mixture of about 1:30 to about 1:0.5.

In some embodiments of the present invention, the pharmaceutical composition of the present invention is an aqueous solution and the pH value of the pharmaceutical composition is from about 5.0 to about 9.0, and preferably from about 6.0 to about 8.0.

In some embodiments of the present invention, the pharmaceutical composition is in a form selected from aqueous solution, lyophilized powder and oral dosage forms.

In some embodiments of the present invention, the pharmaceutical composition further comprises at least one pharmaceutically acceptable excipient.

In some embodiments of the present invention, the pharmaceutical composition is free of polysorbate 80 which may result in diarrhea and hypersensitivity reactions in patients. In some embodiments of the present invention, the pharmaceutical composition of the invention is free of alcohol which may result in intoxication.

In some embodiments of the present invention, the administration of the pharmaceutical composition can be via, for example, an oral route or an injection route. In some embodiments of the present invention, the administration of the pharmaceutical composition is via an intradermal, intramuscular, intraperitoneal, intravenous or subcutaneous injection route.

The prodrug of cabazitaxel of the present invention provides improved aqueous solubility, which enables the pharmaceutical composition with cyclodextrin disclosed in the present invention to have further improved physicochemical properties, so the pharmaceutical composition of the present invention is suitable for injection. The pharmaceutical composition may contain no polysorbate 80 (surfactant) or alcohol, so the pharmaceutical composition of the present invention may result in fewer hypersensitivity reactions than the currently commercially available formulations that contain a polysorbate 80 (surfactant).

The pharmaceutical composition of the present invention also allows administration of cabazitaxel to patients without the need of premedication, that is, administration of an antihistamine and/or corticosteroid (such as dexamethasone or equivalent steroid) and/or H2 antagonist prior to the initiation of the cabazitaxel administration.

The pharmaceutical composition of the present invention may also avoid diarrheal side effect accompanying cabazitaxel administration primarily, if not totally, due to the presence of polysorbate 80 in the currently marketed cabazitaxel injection products.

The pharmaceutical composition of the present invention may also be applicable to develop oral dosage forms comprising a therapeutically effective amount of cabazitaxel for treating a tumor in a patient.

DETAILED DESCRIPTION OF THE PREFERRED EMBODIMENTS

Hereinafter, the present invention will be further illustrated with reference to the following examples. However, these examples are only provided for illustrative purposes, but not to limit the scope of the present invention.

Example 1. Synthesis of Cabazitaxel (CBT) Succinate

Scheme 1. The Synthesis Procedure of CBT Succinate

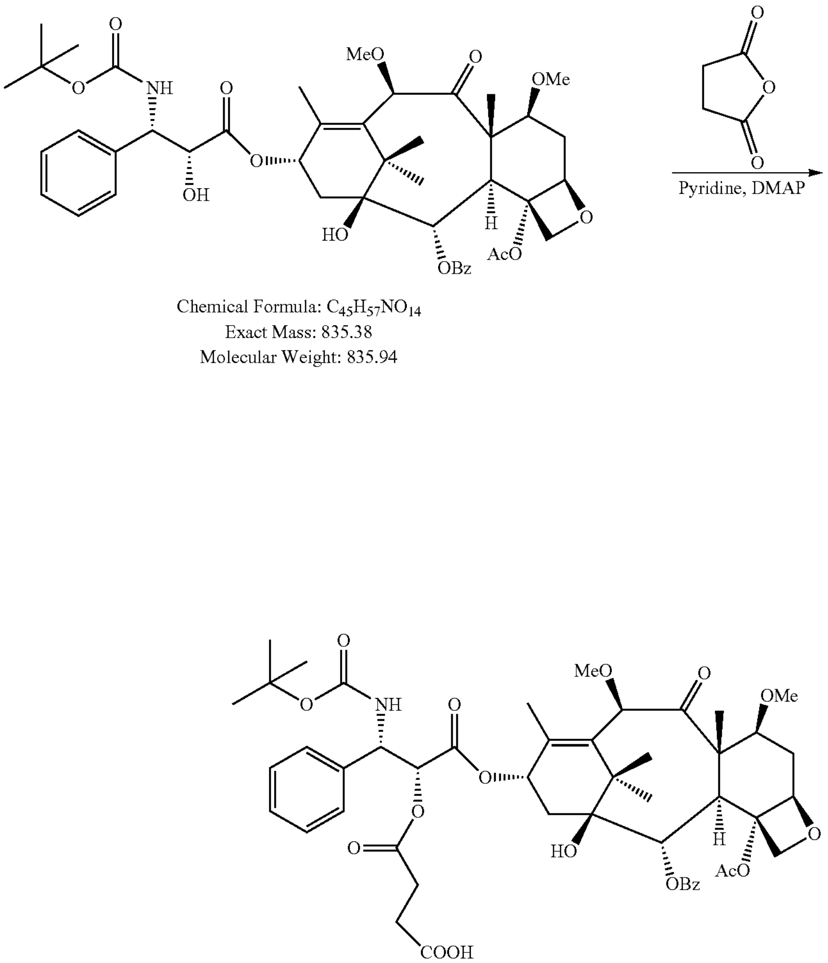

Chemical Formula: $C_{45}H_{57}NO_{14}$
Exact Mass: 835.38
Molecular Weight: 835.94

Chemical Formula: $C_{49}H_{61}NO_{17}$
Exact Mass: 935.39
Molecular Weight: 936.02

Figure 1:
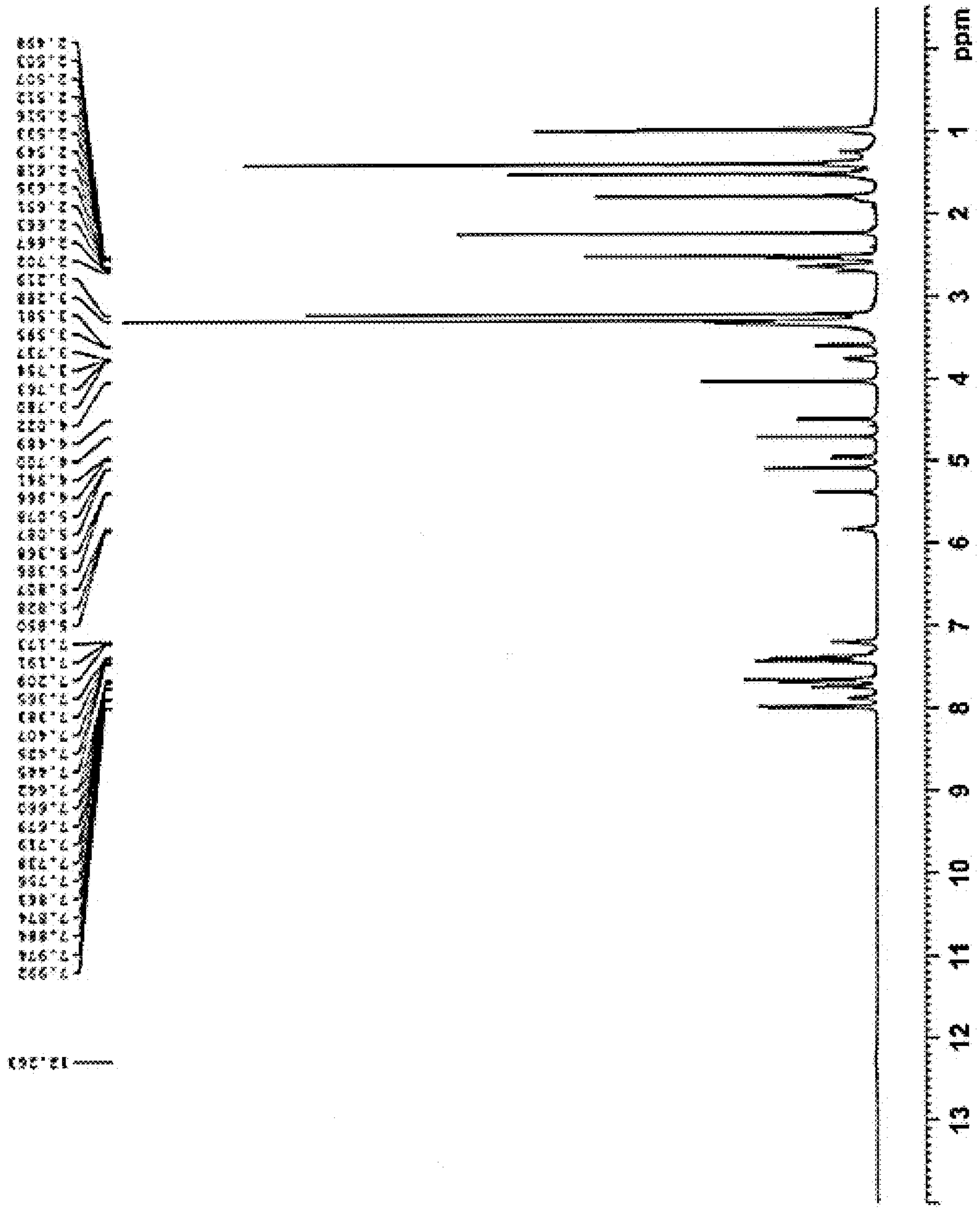
FIG. 1 is $^{1}$H-NMR spectrum of cabazitaxel succinate.
Figure 2:
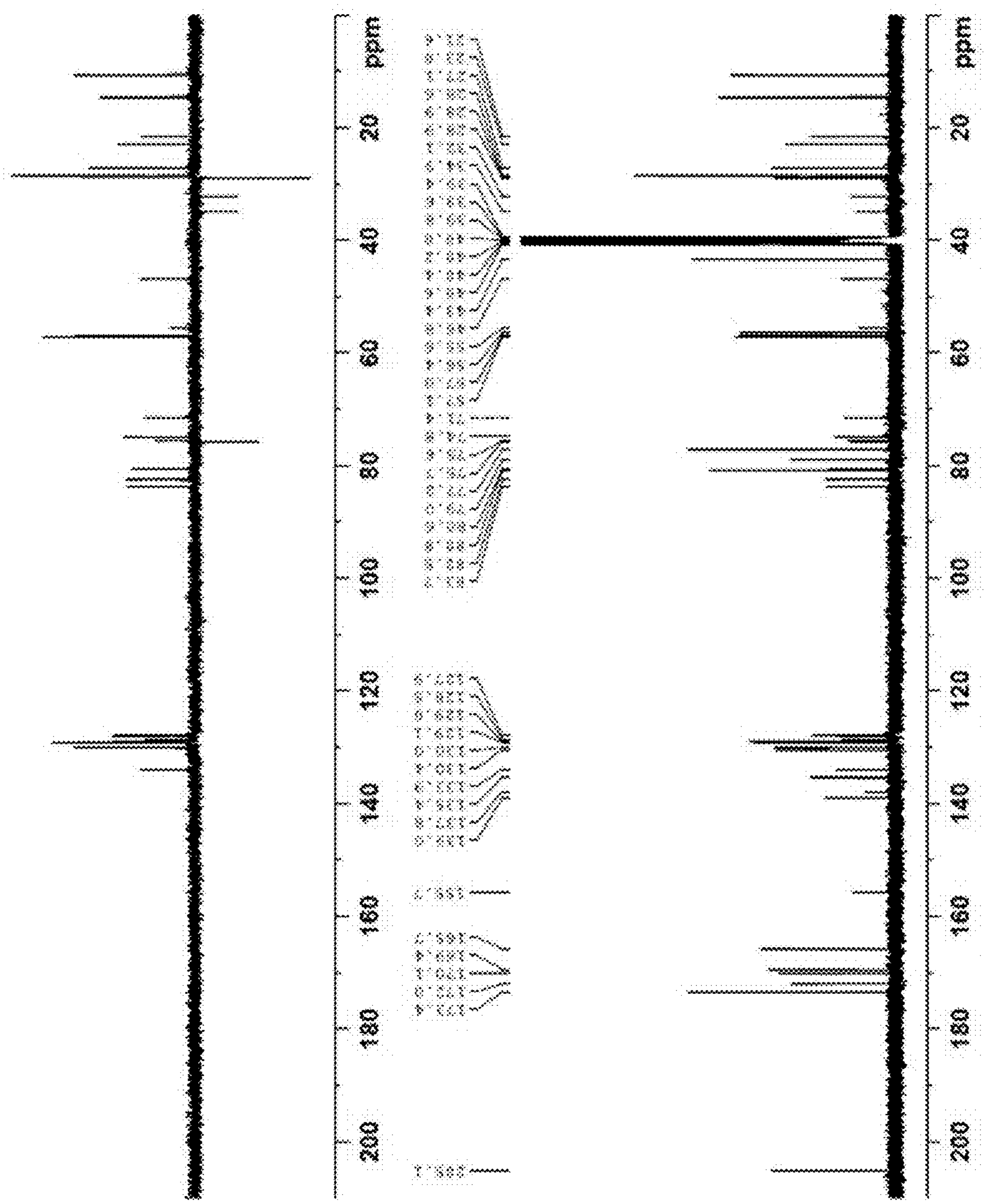
FIG. 2 is DEPT-NMR spectrum of cabazitaxel succinate.

Cabazitaxel (CBT, $C_{45}H_{57}NO_{14}$) (0.2 grams (g), 1 equivalent (equiv.)), pyridine (Py) (5 milliliters (mL)), succinic anhydride (28.8 milligrams (mg), 1.2 equiv.) and 4-dimethylaminopyridine (DMAP) (6 mg, 0.2 equiv.) were added into a 25 mL reactor and reacted at 20 °C to 30 °C for 3.5 hours (h) and the CBT was consumed (monitored by thin layer chromatography (TLC)). The resulting mixture was concentrated to dryness to obtain about 0.3 g crude product. After checked by nuclear magnetic resonance (NMR) spectrum, it was the desired prodrug CBT succinate but containing some DMAP, pyridine and succinic anhydride. The crude product was washed with n-heptane first and succinic anhydride was removed. As it still contained DMAP and trace pyridine, the crude product was dissolved in dichloromethane (DCM) and extracted with 2% citric $acid_{(aq)}$ solution. The organic layer was separated and concentrated to dryness to obtain about 0.15 g of CBT succinate. $^1$H-NMR spectrum and DEPT-NMR spectrum of cabazitaxel succinate are shown in FIG. 1 and FIG. 2, respectively.

Example 2. Synthesis of Cabazitaxel (CBT) Phosphate

Scheme 2. The Synthesis Procedure of CBT Phosphate

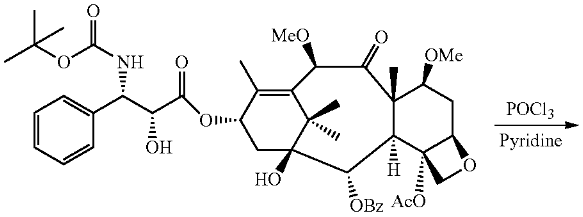

Chemical Formula: $C_{45}H_{57}NO_{14}$
Exact Mass: 835.38
Molecular Weight: 835.94

-continued

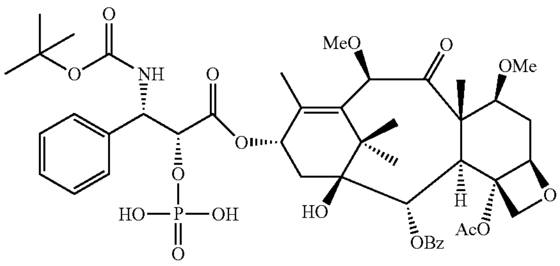

Chemical Formula: $C_{45}H_{58}NO_{17}P$
Exact Mass: 915.34
Molecular Weight: 915.92

Figure 3:
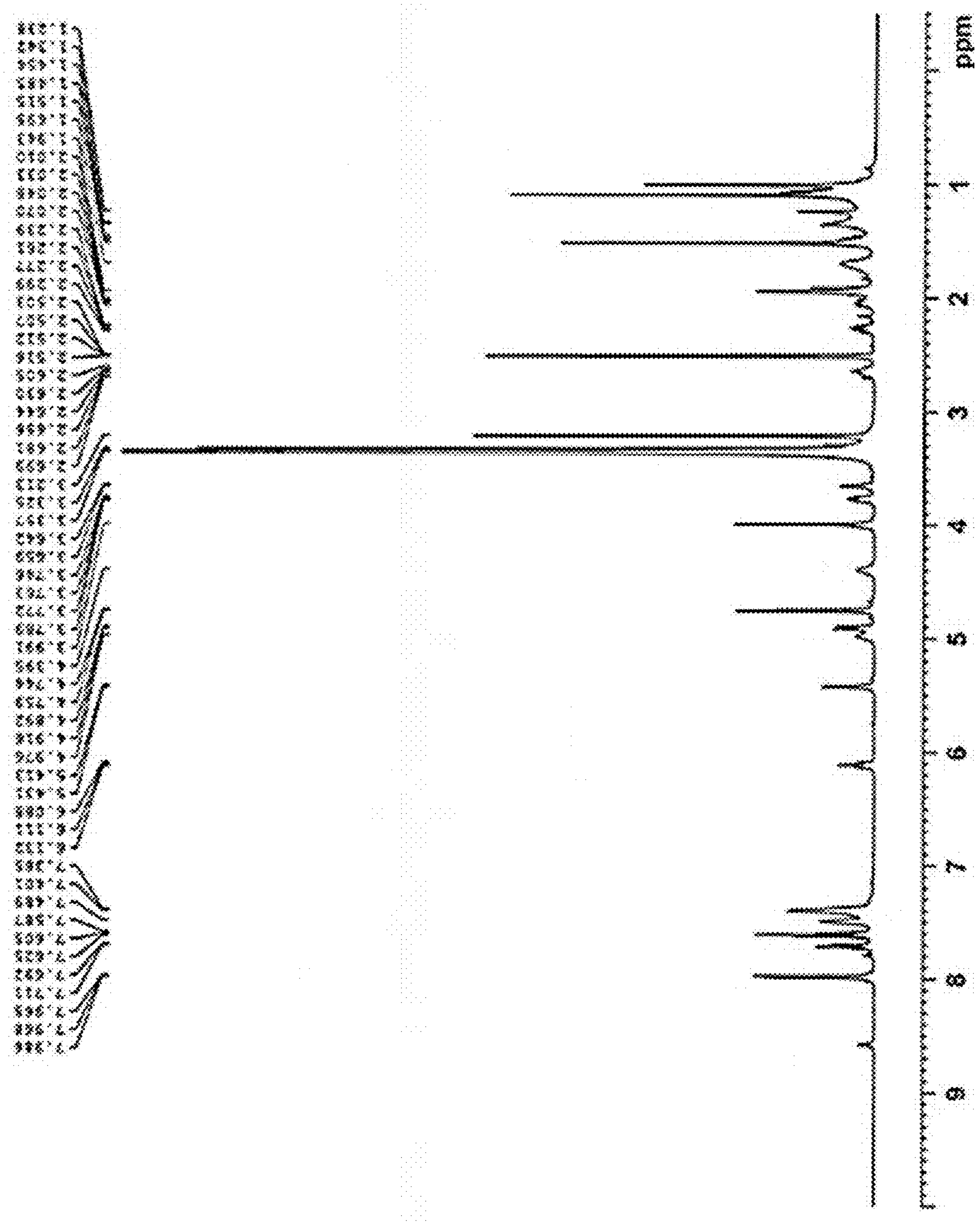
FIG. 3 is $^{1}$H-NMR spectrum of cabazitaxel phosphate.
Figure 4:
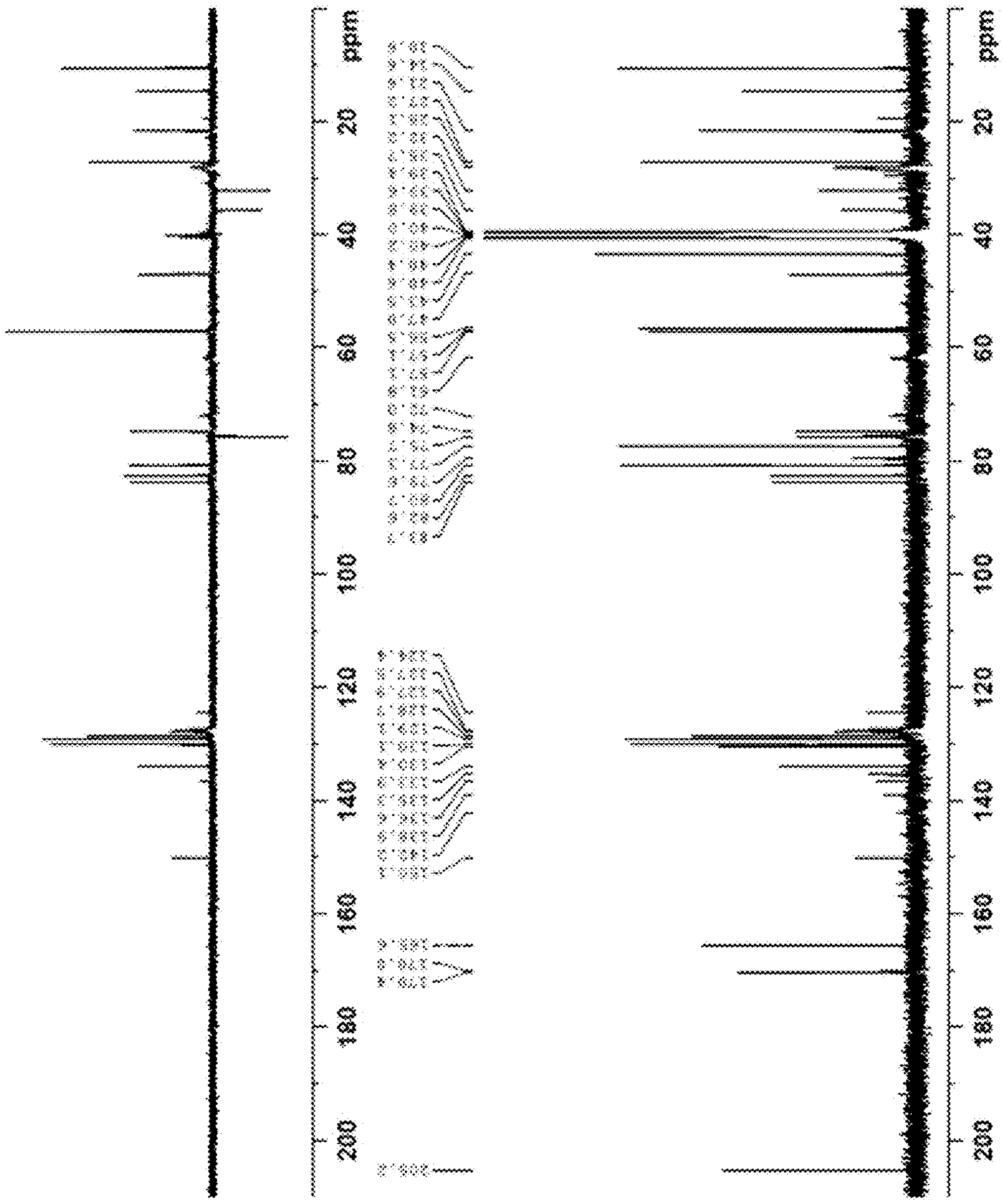
FIG. 4 is DEPT-NMR spectrum of cabazitaxel phosphate.

Cabazitaxel (0.2 g, 1 equiv.), pyridine (5 mL, 25 vol.) and phosphorus oxide trichloride ($POCl_3$) (90 mg, 2.45 equiv.) was added into a 25 mL reactor and reacted at 20 °C to 30 °C for 3 hours. The resulting mixture was extracted with methyl isobutyl ketone (MIBK) and 5N HCl, subsequently. The organic layer was concentrated to obtain 0.4 g of off-white solid (pyridine was still contained). This solid was further purified by silica gel column chromatography and about 0.23 g product CBT phosphate was obtained with a 52.67% yield. $^1$H-NMR spectrum and DEPT-NMR spectrum of cabazitaxel phosphate are shown in FIG. 3 and FIG. 4, respectively.

Figure 5:
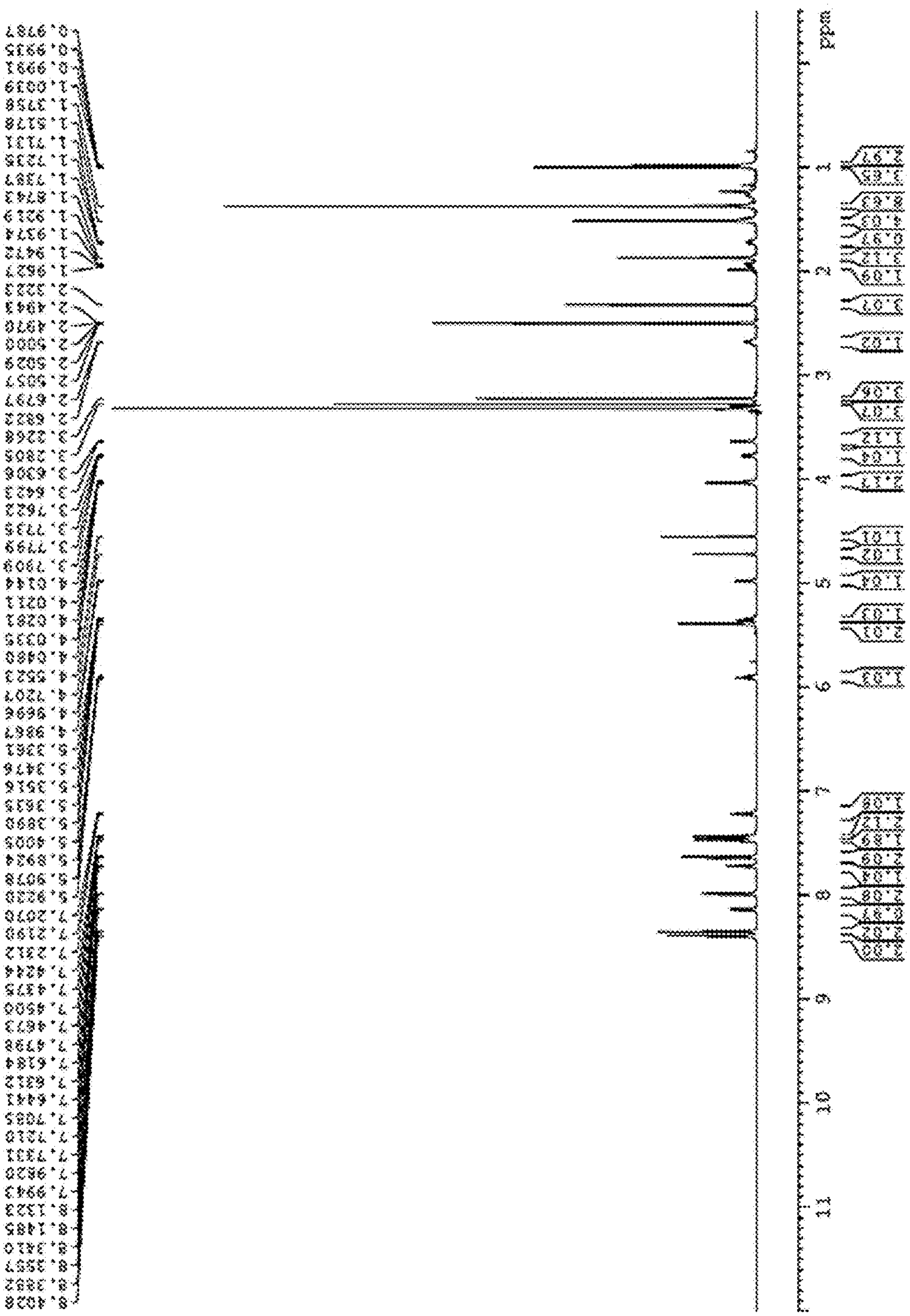
FIG. 5 is $^{1}$H-NMR spectrum of cabazitaxel para-nitrobenzoate (X=para-$NO_2$).
Figure 6:
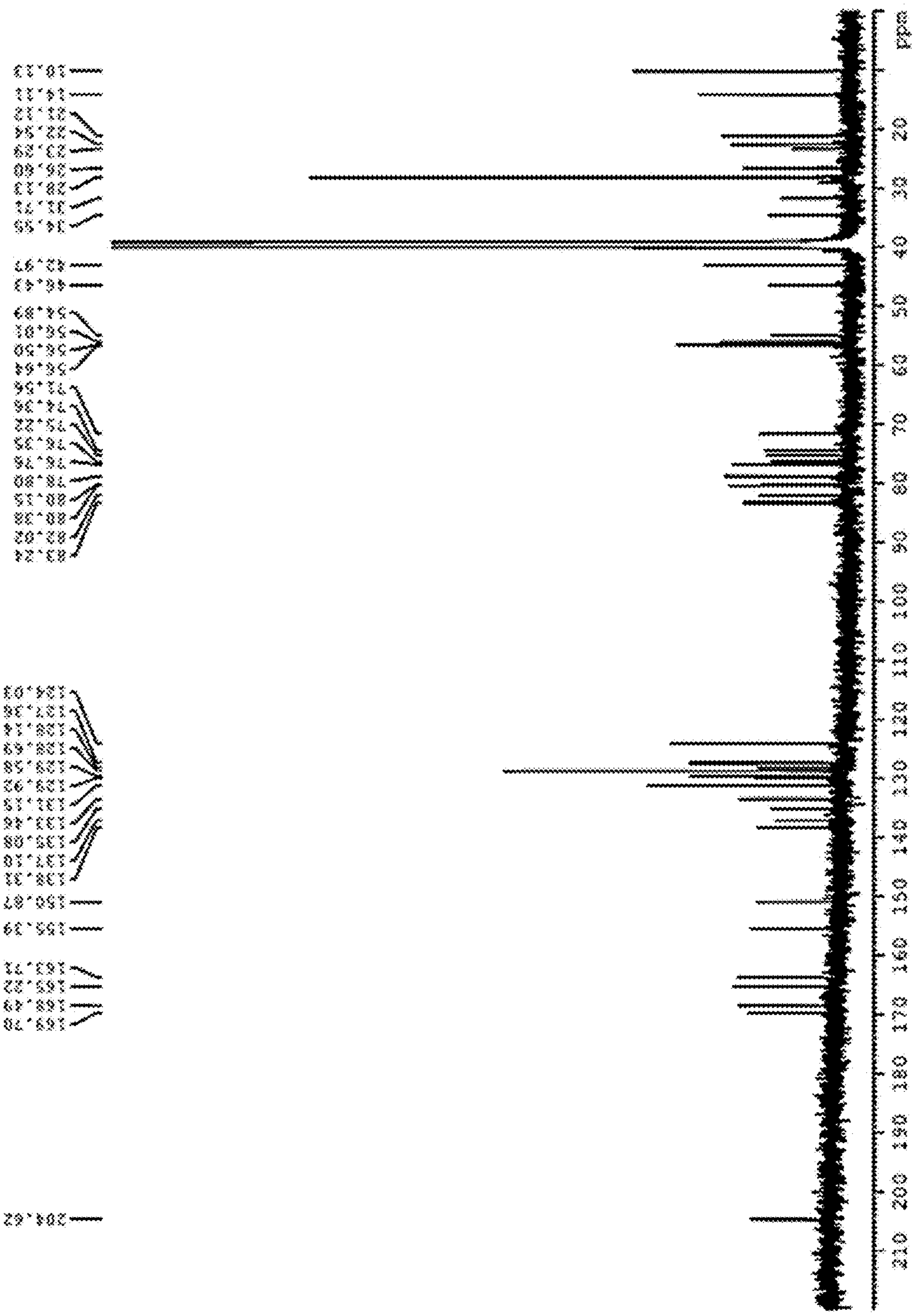
FIG. 6 is $^{13}$C-NMR spectrum of cabazitaxel para-nitrobenzoate (X=para-$NO_2$).

Example 3. Synthesis of Cabazitaxel (CBT) Nitrobenzoates and Cabazitaxel (CBT) Benzoate A solution of 4-nitrobenzoic acid (47.98 mg, 0.29 mmole) in dry dichloromethane (DCM) (5 mL) was prepared, to which 4-dimethylaminopyridine (DMAP, 5.8 mg, 0.047 mmole) and N,N'-diisopropylcarbodiimide (DIC, 36 mg, 0.29 mmole) were added. The resulting mixture was stirred for 10 minutes. Subsequently, cabazitaxel (200 mg, 0.24 mmole) dissolved in dry DCM (5 mL) was added to the above mixture and stirred for an additional 3 hours. The reaction mixture was then evaporated under vacuum to remove the solvent, and the resulting residue was subjected to purification by column chromatography using silica gel and a mobile phase consisting of 1% methanol in DCM. This purification process afforded CBT 4-nitrobenzoate (i.e., CBT para-nitrobenzoate), yielding 97.7 mg (41%) of white solids. $^1$H-NMR spectrum and 1$^3$C-NMR spectrum of cabazitaxel para-nitrobenzoate are shown in FIG. 5 and FIG. 6, respectively.

Figure 7:
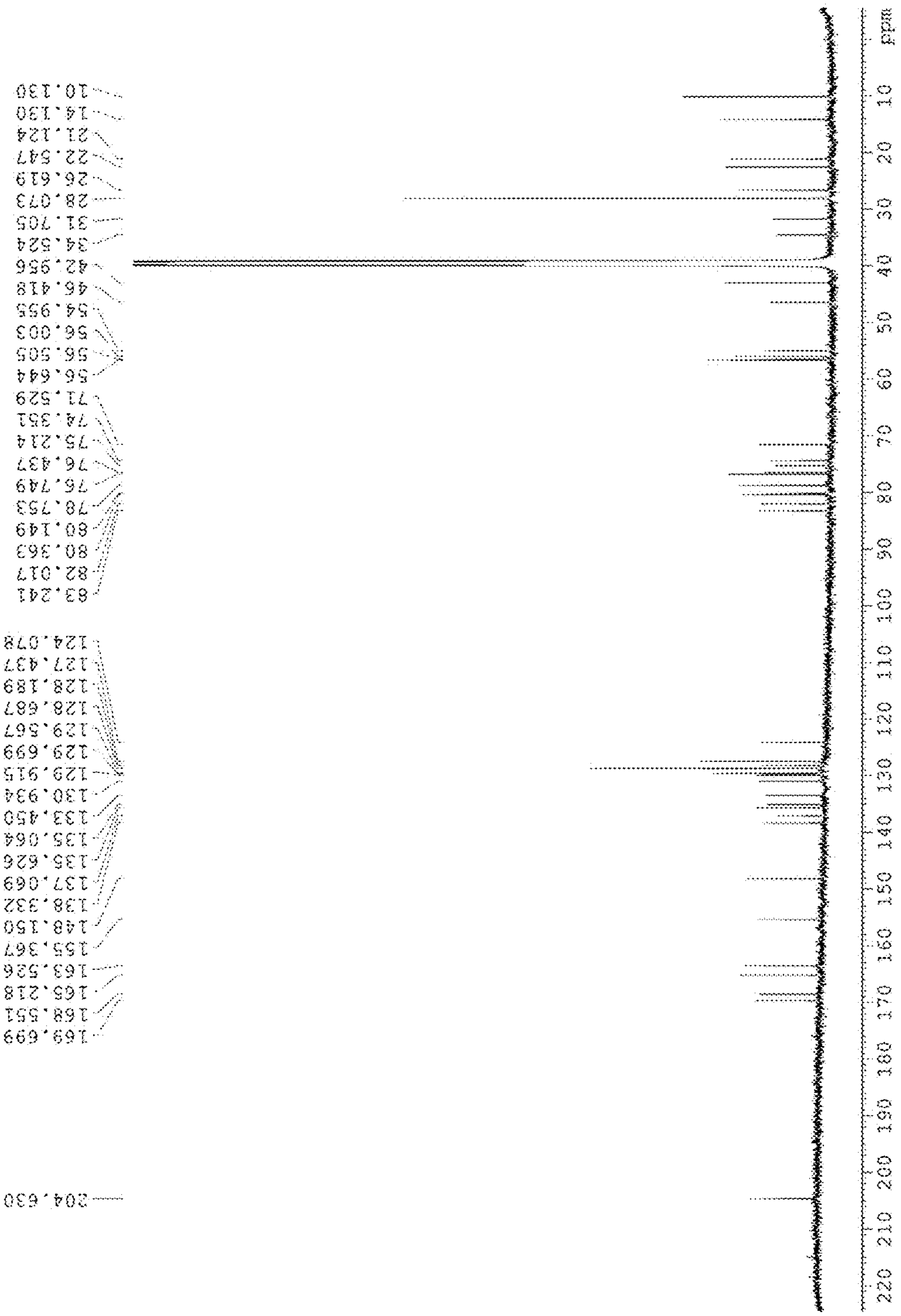
FIG. 7 is 150 CMR spectrum of cabazitaxel meta-nitrobenzoate (X=meta-$NO_2$).
Figure 8:
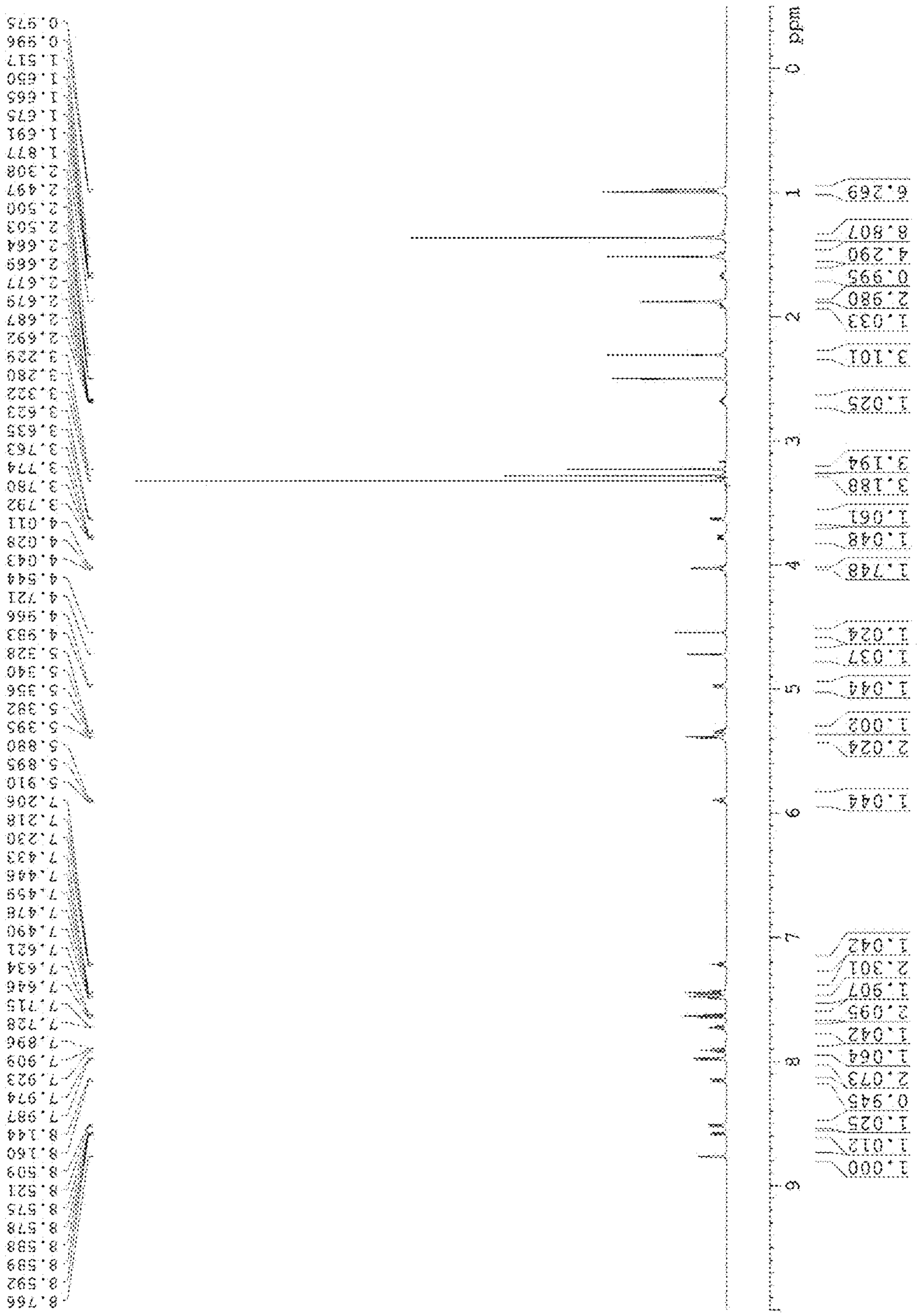
FIG. 8 is 600 PMR spectrum of cabazitaxel meta-nitrobenzoate (X=meta-$NO_2$).
Figure 9:
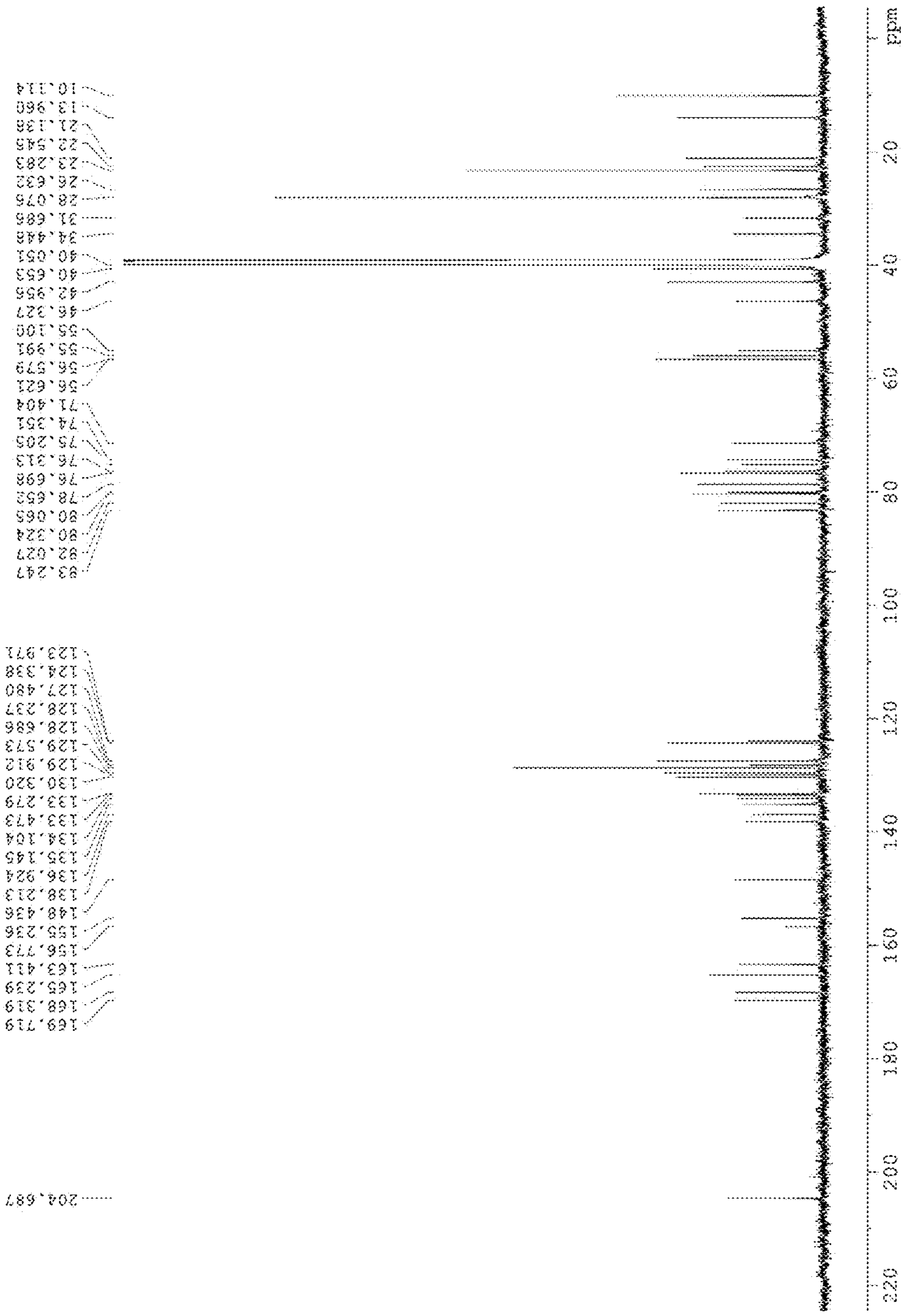
FIG. 9 is 150 CMR spectrum of cabazitaxel ortho-nitrobenzoate (X=ortho-$NO_2$).
Figure 10:
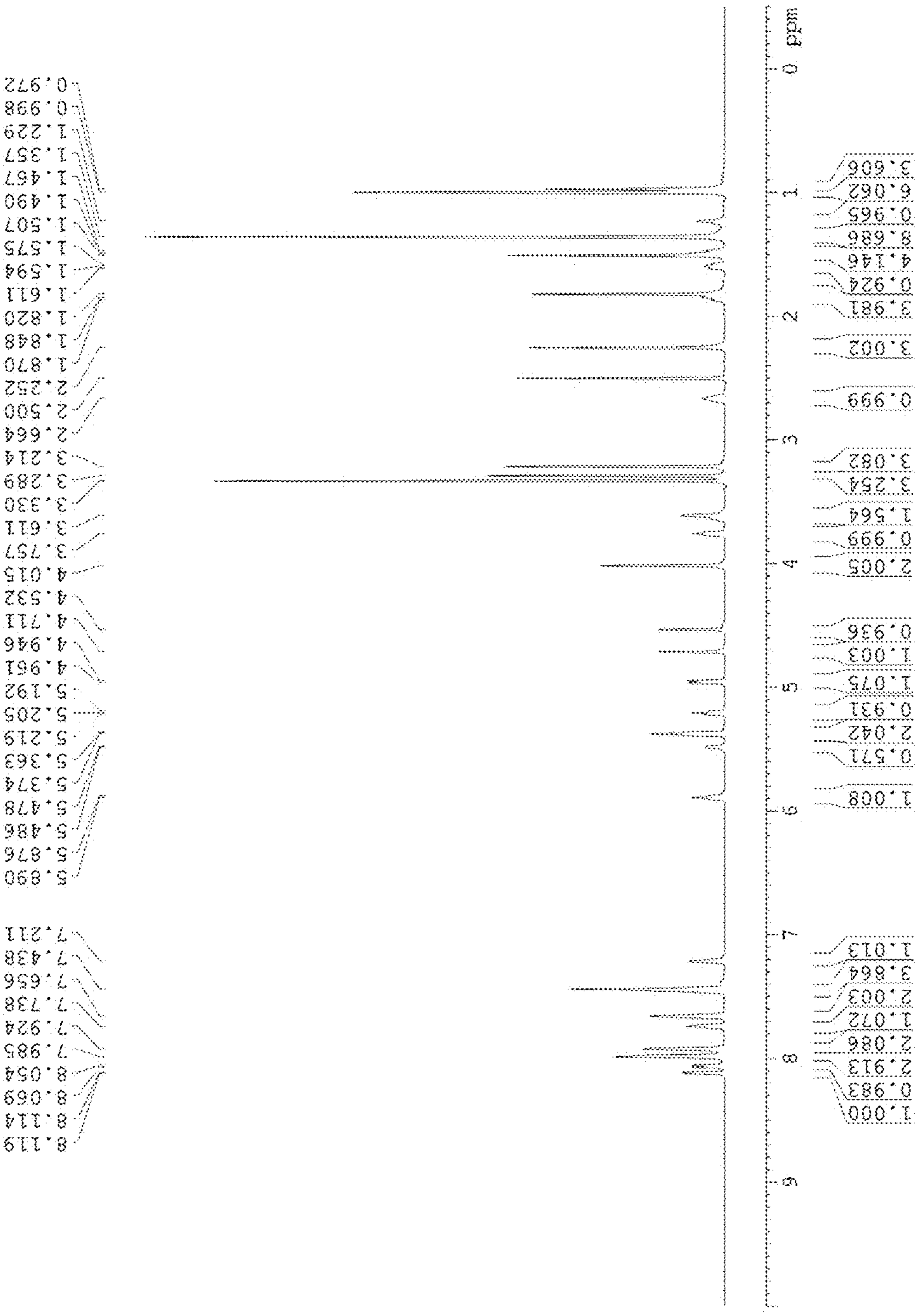
FIG. 10 is 600 PMR spectrum of cabazitaxel ortho-nitrobenzoate (X=ortho-$NO_2$).
Figure 11:
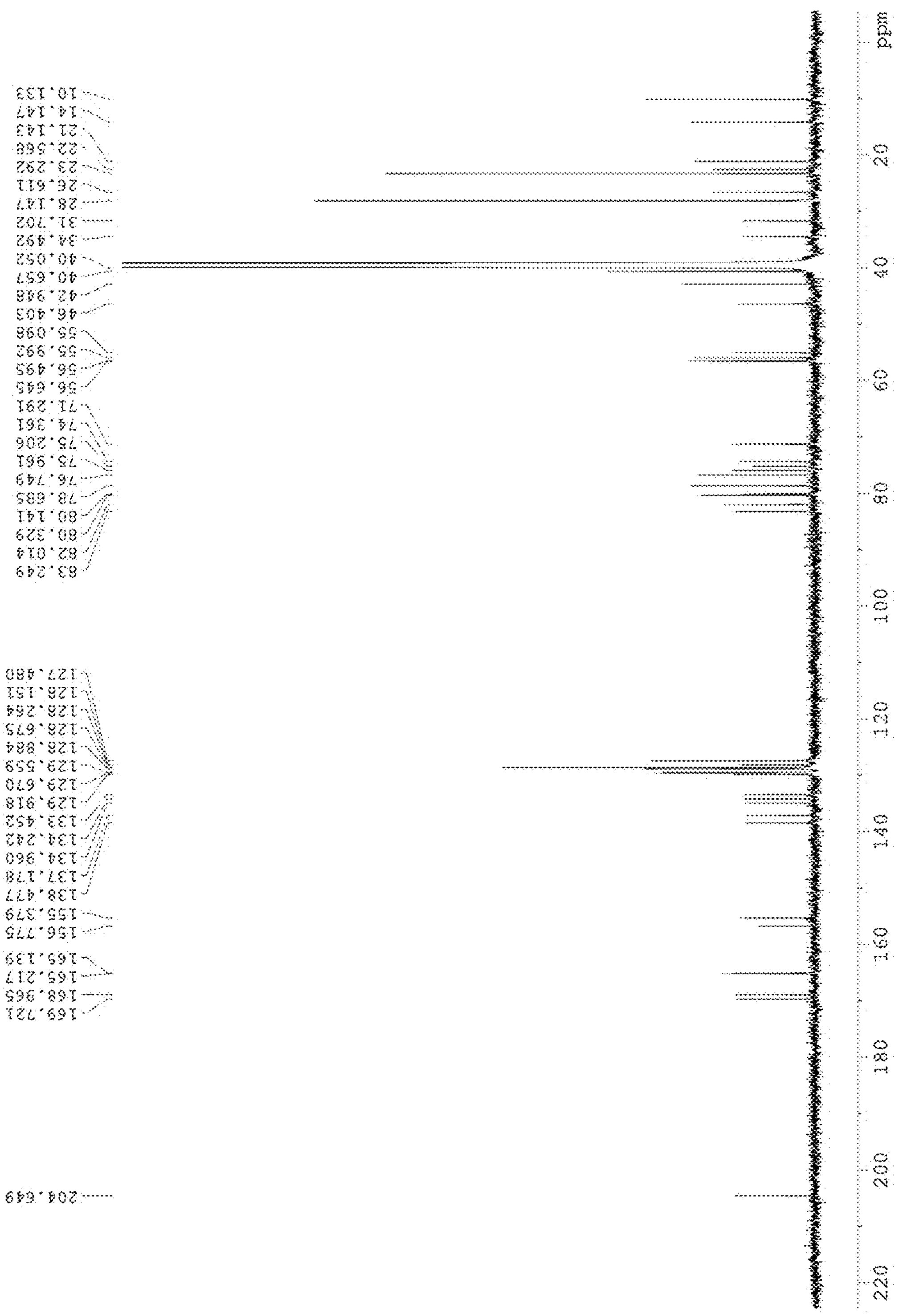
FIG. 11 is 150 CMR spectrum of cabazitaxel benzoate (X=H).
Figure 12:
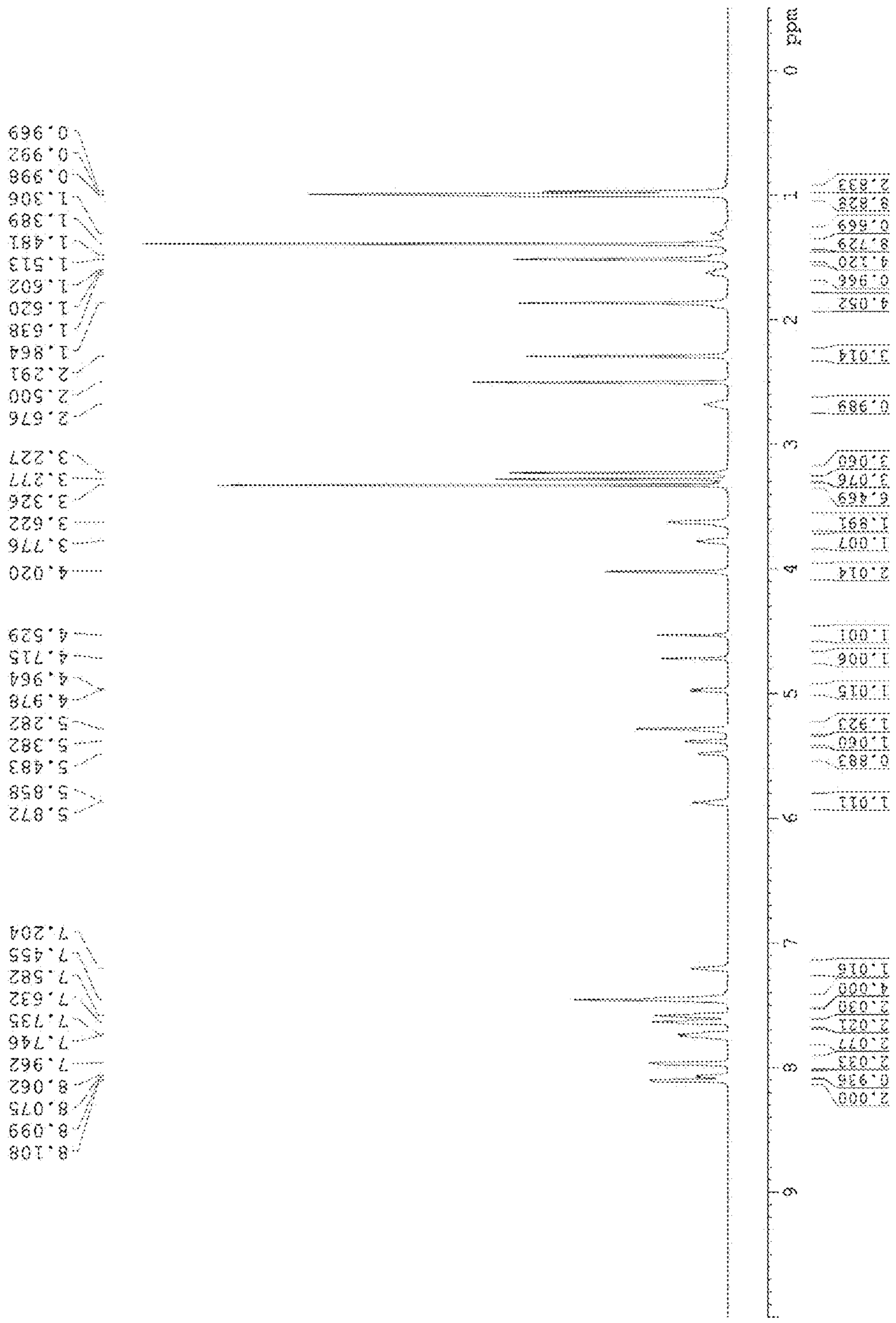
FIG. 12 is 600 PMR spectrum of cabazitaxel benzoate (X=H).

In addition, CBT 2-nitrobenzoate (i.e., CBT ortho-nitrobenzoate), CBT 3-nitrobenzoate (i.e., CBT meta-nitrobenzoate) and CBT benzoate can be synthesized by the same method described in this example. 150 CMR spectrum and 600 PMR spectrum of cabazitaxel meta-nitrobenzoate are shown in FIG. 7 and FIG. 8, respectively. 150 CMR spectrum and 600 PMR spectrum of cabazitaxel ortho-nitrobenzoate are shown in FIG. 9 and FIG. 10, respectively. 150 CMR spectrum and 600 PMR spectrum of cabazitaxel benzoate are shown in FIG. 11 and FIG. 12, respectively.

Example 4. Preliminary Evaluation of In Vivo Bioconversion of Cabazitaxel (CBT) Succinate To evaluate whether CBT succinate could be quickly hydrolyzed and release the parent drug, CBT, after intrave- Scheme 3. The Synthesis Procedure of CBT Para-nitrobenzoate

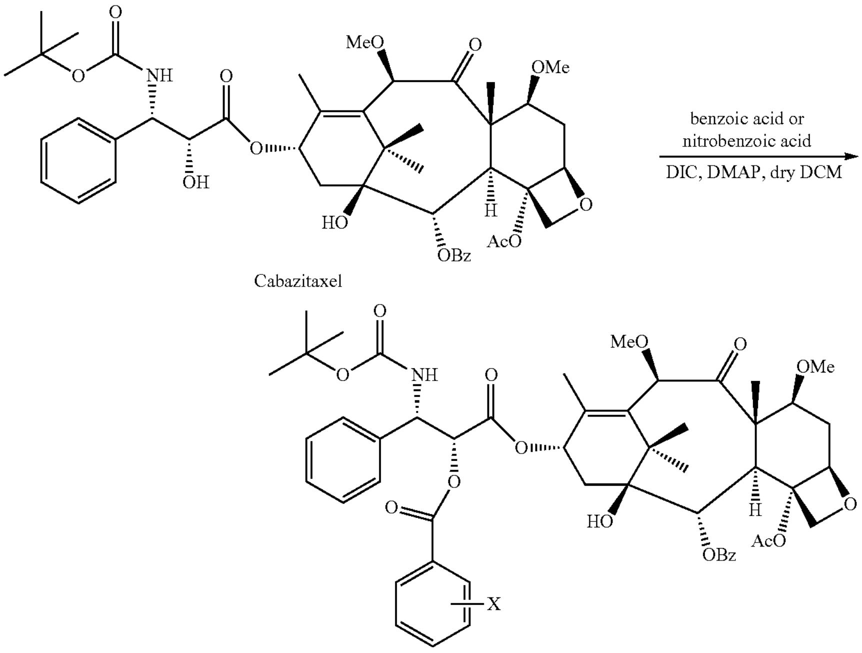

Cabazitaxel

X = H
X = otho-$NO_2$,
X = meta-$NO_2$,
X = para-$NO_2$ nous (IV) injection, CBT succinate was dissolved in a preclinical formulation (50% PEG300 in normal saline) and dosing at 15 milligrams per kilogram of body weight (mg/kg) IV in six ICR male mice and blood collection was carried out at specific time points. Since some blood collection time points were close, the mice were grouped into two (three mice for each group) and blood collection was carried out alternately by the two groups. Blood was collected in tubes coated with lithium heparin via facial vein (100 microliters (μL)) or cardiac puncture (300 μL) from anesthetized mice, mixed gently, then kept on ice and centrifuged at 2,500×g for 15 minutes (min) at 4 °C, within 1 hour of collection. The plasma was then harvested and kept frozen at −70 °C until further processing. The plasma samples were thawed and processed using acetonitrile precipitation and analyzed by liquid chromatography mass spectrometry (LC-MS)/MS (SCIEX 5500+) with the parameters listed below:

Column: Agilent Poroshell 120 EC-C18 column 2.7 μm;

Temperature: 40 °C;

Flow rate: 500 μL/min;

Mobile phase A: acetonitrile (ACN)/formic acid (FA) =100/0.2 (v/v); and

Mobile phase B: water/FA=100/0.2 (v/v).

From 0 min to 1 min, mobile phase A was 20%, and mobile phase B was 80%; from 1 min to 2 min, mobile phase A was 70%, and mobile phase B was 30%; and from 2 min to 3 min, mobile phase A was 20%, and mobile phase B was 80%.

In addition, a plasma calibration curve of the test compound was generated for concentration determination.

The bioanalysis results are tabulated as Tables 1 to 3 below. The values of mean and standard deviation (SD) are calculated. BLOQ means "below the limit of quantification", and N/A means "not available". Normal saline used herein is 0.90% sodium chloride aqueous solution.

TABLE 1

The exposure levels of CBT succinate in mouse plasma samples - CBT Succinate in 50% PEG300 formulation (15 mg/kg, IV) group:

| Time (h) | CBT succinate concentration (ng/mL) | | | Mean | SD |
|---|---|---|---|---|---|
| 0.083 | 5975 | 5803 | 5480 | 5753 | 251 |
| 0.167 | 3102 | 3144 | 2857 | 3034 | 155 |
| 0.5 | 541 | 397 | 221 | 386 | 160 |
| 1 | 25 | 51 | 73 | 50 | 24 |
| 2 | BLOQ | 15 | BLOQ | 15 | N/A |
| 4 | BLOQ | BLOQ | BLOQ | BLOQ | N/A |
| 8 | BLOQ | BLOQ | BLOQ | BLOQ | N/A |
| 24 | BLOQ | BLOQ | BLOQ | BLOQ | N/A |

TABLE 2

The exposure levels of Cabazitaxel in mouse plasma samples - CBT succinate in 50% PEG300 formulation (15 mg/kg, IV) group:

| Time (h) | CBT concentration (ng/mL) | | | Mean | SD |
|---|---|---|---|---|---|
| 0.083 | 6359 | 6070 | 6126 | 6185 | 153 |
| 0.167 | 3371 | 3249 | 2664 | 3095 | 378 |
| 0.5 | 562 | 369 | 248 | 393 | 158 |
| 1 | 36 | 37 | 57 | 43 | 12 |
| 2 | 52 | 29 | 48 | 43 | 12 |
| 4 | 18 | 26 | 40 | 28 | 11 |
| 8 | BLOQ | 17 | BLOQ | 17 | N/A |
| 24 | BLOQ | BLOQ | BLOQ | BLOQ | N/A |

TABLE 3

The PK parameters of CBT succinate and CBT after administering CBT succinate as in 50% PEG300 formulation (15 mg/kg, IV) in mouse plasma samples

| CBT Succinate 15 mg/kg, IV | | CBT Succinate | CBT |
|---|---|---|---|
| $t_{1/2}$ | (h) | 0.23 | 4.92 |
| $C_0$ | (ng/mL) | 10826 | 12259 |
| AUClast | (h*ng/mL) | 1768 | 2049 |
| AUCInf | (h*ng/mL) | 1773 | 2170 |
| AUC/D | (h*kg*ng/mL/mg) | 118 | 162 |
| AUC Extr | (%) | 0.28 | 5.56 |
| MRT | (h) | 0.16 | 1.30 |
| Vss | (L/kg) | 1.38 | 8.04 |
| CL | (mL/min/kg) | 141.01 | 102.94 |

The pharmacokinetics (PK) parameters listed in Table 3 include:

1. $t_{1/2}$: Apparent terminal elimination half-life;
2. $C_0$: Initial concentration;
3. AUClast: Area under the plasma concentration-time curve (AUC) from the time of dosing to the time of the last measurable concentration;
4. AUCInf: AUC from time of dosing extrapolated to infinity;
5. AUC/D: AUC divided by dose;
6. AUC Extr: AUC extrapolated from last time point to infinity as a percentage of total AUC;
7. MRT: The average time a drug molecule stays in the body. It's calculated by summing the total time each molecule spends in the body and dividing by the number of molecules.
8. Vss: Apparent volume of distribution at steady state; and
9. CL: Apparent total body clearance of the drug from plasma.

The results clearly demonstrated that the bioconversion of CBT succinate to CBT happened very rapidly. In fact, the inventors found that CBT succinate is prone to hydrolysis when dissolved in the aqueous preclinical formulation. This suggests that a pharmaceutical formulation that can protect CBT succinate from pre-mature hydrolysis in the formulation process, in the drug product, and during preparation upon clinical usage, could be challenging.

Example 5. CBT Succinate-Cyclodextrin (CD) Complexation in Aqueous Phase

To evaluate the potential of using a CD as an excipient for solubilizing and stabilizing CBT succinate, sulfobutyl ether beta cyclodextrin (SBECD), 2-hydroxypropyl-β-cyclodextrin (HPBCD), and 2-hydroxypropyl-γ-cyclodextrin (HPγCD) were selected for formulating five different CDs for a series of aqueous phase screening studies.

Excess amount of CBT succinate was weighted and added to a CD composition and stirred for various durations (to allow complexation and solubilization) to obtain test samples comprising CBT succinate-CD inclusion complex. Before assays for CBT succinate and its hydrolysis product (CBT) were performed, the test samples were filtered through a 0.45 micrometer (μm) PVDF syringe filter, and stored for a predetermined storage time (to allow hydrolysis). After the predetermined storage time, the test samples were subjected to high performance liquid chromatography (HPLC) assay with the parameters listed below to obtain the final concentration (conc.) of CBT succinate and CBT.

Column: Thermo BDS Hypersil C18, 5-μm, 4.5×250 mm, #LC-707;
Temperature: 30 °C;
Flow rate: 1.0 mL/min;
Mobile phase A: 9.26 mM $K_2HPO_4$, pH 7.0; and
Mobile phase B: ACN.

From 0 min to 2 min, mobile phase A was 90%, and mobile phase B was 10%; from 30 min to 30.1 min, mobile phase A was 10%, and mobile phase B was 90%; and from 31 to 39 min, mobile phase A was 90%, and mobile phase B was 10%.

The results from three experiments (with different stirring durations and storage time) were summarized in Table 4 as below.

Both experiments 1 and 2 have demonstrated that β-CDs (SBECD and HPBCD) are a lot more efficient than HPγCD in solubilizing CBT succinate and protect CBT succinate from hydrolysis to CBT.

TABLE 4

Summary for aqueous phase CD screening experiments

| No. | CD composition (% weight) | Stirring duration before 0.45 μm filtration | Storage time before HPLC assay | Final CBT conc. (mg/mL) | Final CBT Succinate conc. (mg/mL) | mol % CBT/ (CBT + CBT Succinate) |
|---|---|---|---|---|---|---|
| 1 | 9% SBECD | 24 h | 7 days | 0.27 | 0.50 | 37.9% |
| | 6% SBECD + 3% HPγCD | | | 0.32 | 0.32 | 53.0% |
| | 4.5% SBECD + 4.5% HPγCD | | | 0.32 | 0.25 | 59.0% |
| | 3% SBECD + 6% HPγCD | | | 0.33 | 0.16 | 68.9% |
| | 9% HPγCD | | | 0.31 | 0.054 | 86.6% |
| 2 | 9% HPBCD | 52 h | 3 days | 0.13 | 1.83 | 7.1% |
| | 6% HPBCD + 3% HPγCD | | | 0.10 | 1.32 | 8.0% |
| | 4.5% HPBCD + 4.5% HPγCD | | | 0.09 | 1.10 | 8.2% |
| | 3% HPBCD + 6% HPγCD | | | 0.07 | 0.86 | 8.8% |
| | 9% HPγCD | | | 0.04 | 0.44 | 10.1% |
| 3 | 9% SBECD | 70 h | 1 h | 0.08 | 1.60 | 5.5% |
| | 6% SBECD + 3% HPBCD | | | 0.09 | 1.69 | 5.5% |
| | 4.5% SBECD + 4.5% HPBCD | | | 0.09 | 1.71 | 5.6% |
| | 3% SBECD + 6% HPBCD | | | 0.11 | 1.82 | 5.8% |
| | 9% HPBCD | | | 0.11 | 1.80 | 6.2% |

Example 6. Preparation of Grinded CBT Succinate-CD Inclusion Complex Crude Product by Hand with Mortar and Pestle For complexing CBT succinate with a CD (either SBECD, HPBCD, HPγCD, or their combinations) at various molar ratios, CBT succinate was mixed with a CD and grinded manually for 1 h to obtain a crude CBT succinate-CD inclusion complex.

Example 7. Preparation of Grinded CBT Succinate-CD Inclusion Complex Crude Product by Ball Milling Homogenizer For complexing CBT succinate with a CD (either SBECD, HPBCD, HPγCD, or their combinations) at various molar ratios, CBT succinate was mixed with a CD and grinded by a BeadBug 6 Microtube Homogenizer at 4,200 rpm using stainless steel milling beads having a diameter of 2.8 millimeters (mm) to obtain a crude CBT succinate-CD inclusion complex.

Example 8. Purification of Grinded CBT Succinate-CD Inclusion Complexes

To efficiently purify the crude CBT succinate-CD inclusion complexes obtained in Examples 6 and 7, the crude CBT succinate-CD inclusion complexes were dissolved in a phosphate buffer or a citric acid-$Na_2HPO_4$ buffer (at pH 5, 6, 7, or 8) then filtered through a 0.45 μm PVDF membrane. The resulting solutions of CBT succinate-CD inclusion complexes were further lyophilized to obtain a stable CBT succinate-CD inclusion complex lyo cakes. These lyo cakes were loose and could be broken up into lyo powder easily. The lyo cake or powder could be dissolved easily.

CBT and CBT succinate content in the mixtures of starting materials and the complexed and purified CBT succinate-CD inclusion complex lyo cakes were analyzed by HPLC assay as described in Example 5. The content of CBT (the hydrolyzed product of CBT succinate, also the parent drug) was also analyzed, and mol % CBT/(CBT+CBT succinate) was calculated in accordance with the final concentration and molecular weight of CBT and CBT succinate, as an indicator for product stability.

The results of an array of representative CBT succinate-CD inclusion complexes are summarized in Table 5 below. The active pharmaceutical ingredient (API) in Table 5 is CBT succinate, so the "Starting % API" indicates the original percent of CBT succinate in the mixture of CBT succinate and CD (before complexation), and the "% API in lyo cake" indicates the percent of CBT succinate ending up in the lyo cake after complexation and purification. They are expressed as weight percent. Small difference between "Starting % API" and "% API in lyo cake" means the formation of the inclusion complex is probably very efficient. Easy 0.45 μm filtration suggests that there is very limited agglomerated inclusion complex or CBT succinate/CBT precipitates that could be filtered out as loss. From above, it can be found that the entire inclusion complex formation and purification process is highly efficient and the overall yield is high.

For the results of "Ease of 0.45 μm filtration", "easy" means the filtering was completed without any obstruction; "okay" means the filtering was completed with slight obstruction; "difficult" means the filtering was completed with replaced filters due to obstruction; and "very difficult" means the filtering could not be completed due to serious obstruction.

TABLE 5

Summary of representative experiments for purification of CBT Succinate-CD inclusion complexes

| CBT Succinate - CD (Starting Materials Molar Ratio) | Grinding | Buffer for dissolving | pH after dissolving | Ease of 0.45 μm filtration | % API in lyo powder | Starting % API | mol % CBT/ (CBT + CBT Succinate) |
|---|---|---|---|---|---|---|---|
| CBT Succinate:SBECD = 1:1.1 | Hand, 1 h | 20 mM Phosphate buffer, pH 8.0 | 6.90 | Easy | 21.9% | 29.2% | 6.65% |
| CBT Succinate:SBECD = 1:1.1 | Beads, 4,200 rpm 90 s × 3 | 20 mM Phosphate buffer, pH 8.0 | 7.07 | Easy | 22.9% | 29.2% | 8.14% |
| CBT Succinate:SBECD = 1:1.1 | Beads, 4,200 rpm 90 s × 3 | Citric acid - $Na_2HPO_4$ buffer (pH 7.0)* | 6.83 | Okay | 5.7% | 29.2% | 8.86% |
| CBT Succinate:SBECD = 1:1.1 | Beads, 4,200 rpm 90 s × 3 | Citric acid - $Na_2HPO_4$ buffer (pH 6.0)* | 5.83 | difficult | 3.4% | 29.2% | 4.69% |
| CBT Succinate:SBECD = 1:1.1 | Beads, 4,200 rpm 90 s × 3 | Citric acid - $Na_2HPO_4$ buffer (pH 5.0)* | 4.91 | Very difficult | 1.0% | 29.2% | 4.18% |
| CBT Succinate:HPBCD= 1:2.2 | Beads, 4,200 rpm 90 s × 3 | 20 mM Phosphate buffer, pH 8.0 | 6.95 | Easy | 19.6% | 22.5% | 7.42% |
| CBT Succinate:HPBCD = 1:2.2 | Beads, 4,200 rpm 90 s × 3 | Citric acid - $Na_2HPO_4$ buffer (pH 7.0)* | 6.92 | Easy | 10.0% | 22.5% | 12.48% |
| CBT Succinate:HPBCD = 1:2.2 | Beads, 4,200 rpm 90 s × 3 | Citric acid - $Na_2HPO_4$ buffer (pH 6.0)* | 5.90 | difficult | 9.6% | 22.5% | 5.90% |
| CBT Succinate:HPBCD = 1:2.2 | Beads, 4,200 rpm 90 s × 3 | Citric acid - $Na_2HPO_4$ buffer (pH 5.0)* | 5.03 | Very difficult | 2.5% | 22.5% | 4.84% |

*Specified pH buffers were prepared by mixing x mL of 0.1M-citric acid and y mL 0.2M-$Na_2HPO_4$ per Merck Buffer Reference Center: "CITRIC ACID - $NA_2HPO_4$ BUFFER PREPARATION, PH 2.6-7.6"

When the crude CBT succinate-CD inclusion complex was dissolving at a reasonable concentration (at a few % CD), pH dependent solubility was quickly observed. It also appeared that 20 mM phosphate buffer, pH 8.0 provides the best results, as indicated by multiple indicators: 1) ease of 0.45 μm filtration, 2) highest % API in lyo-powder, and 3) lowest mol % CBT/(CBT+CBT succinate). It is speculated that this may relate to the pKa of CBT succinate, which affects the overall dissolving behavior of the CBT Succinate-CD inclusion complex.

Example 9. Dilution Stability of the CBT Succinate-CD Inclusion Complexes

Considering clinical practice of CBT dosing (as described in Jevtana Kit label, Section 2. DOSAGE AND ADMINISTRATION) that "the concentration of the JEVTANA final infusion solution should be between 0.10 mg/mL and 0.26 mg/mL" due to potential infusion related adverse events, it is preferred if the CBT succinate-CD inclusion complex of the present invention demonstrates acceptable in-use stability when it is diluted to concentrations equivalent to CBT between 0.10 mg/mL and 0.26 mg/mL (i.e., CBT succinate between 0.112 mg/mL and 0.291 mg/mL).

CBT succinate-CD inclusion complex lyo cakes were prepared by the ball milling process described in Example 7, and the dissolving (in 20 mM phosphate buffer, pH 8.0) and purifying processes described in Example 8. A dilution stability study was conducted by weighing required amount of the above-mentioned CBT succinate-CD inclusion complex lyo cakes, diluting them with normal saline to the target concentrations, and holding the resulting solution at a predetermined time at room temperature (RT) or at a temperature between 2 °C and 8 °C. At designated time points, the diluted CBT succinate-CD inclusion complex samples were filtered through a 0.22 μm syringe filter to remove any potential insoluble materials (as described in Jevtana Kit label, Section 2.6 Administration) that "Use an in-line filter of 0.22 micrometer nominal pore size during administration". The resulting CBT succinate-CD inclusion complex solution is the "Finished Product" in Table 6. After that, the final concentrations of CBT succinate and CBT were determined by HPLC assay as described in Example 5. In Table 6, the "Starting Materials Molar Ratio" indicates the original ratio of CBT succinate and CD before complexation, and the "Finished Product Molar Ratio" indicates the final ratio of CBT succinate and CD after complexation and purification.

The results are summarized in Table 6 as below.

TABLE 7

Long-term aqueous stability of the CBT succinate-CD inclusion complexes at 2°C to 8 °C

| | Day 0 conc. (mg/g) | Day 14 conc. (mg/g) | Day 21 conc. (mg/g) | Day 28 conc. (mg/g) | Day 35 conc. (mg/g) |
|---|---|---|---|---|---|
| 1:1.1 SBECD | 4.71 | 4.64 | 4.73 | — | — |
| 1:2.2 HPBCD | 7.89 | 7.81 | 7.80 | 7.56 | — |
| 1:1.1 SBECD:1.1 HPBCD | 7.85 | 7.66 | 7.25 | — | — |
| 1:2.2 SBECD | 7.84 | 7.61 | 7.68 | 7.92 | 7.75 |
| 1:2.2 SBECD (saturated) | 11.11 | 11.19 | 11.10 | — | 11.22 |

For the CBT succinate-SBECD (1:2.2), a saturation test was further carried out. Excess amount of the CBT succinate-SBECD (1:2.2) was dissolved by 20 mM pH 8.0 phosphate buffer to test its solubility, and it was found that the inclusion complex enhanced CBT succinate water solubility from 0.120 mg/mL to over 11 mg/mL.

TABLE 6

Summary of dilution stability studies

| CBT Succinate - CD (Starting Materials Molar Ratio) | CBT Succinate - CD (Finished Product Molar Ratio)* | Target concentration (mg/mL) | Hold time before 0.22 μm filtration (h)/ temperature | Final CBT conc. (mg/g) | Final CBT Succinate conc. (mg/g) | mol % CBT/ (CBT + CBT Succinate) |
|---|---|---|---|---|---|---|
| 1:2.2 SBECD | 1:2.5 SBECD | 0.291 | 1/RT | 0.011 | 0.294 | 4.08 |
| 1:2.2 SBECD | 1:2.5 SBECD | 0.112 | 1/RT | 0.004 | 0.111 | 3.86 |
| 1:2.2 SBECD | 1:2.5 SBECD | 0.291 | 16/RT | 0.015 | 0.290 | 5.64 |
| 1:2.2 SBECD | 1:2.5 SBECD | 0.112 | 16/RT | 0.006 | 0.111 | 5.42 |
| 1:2.2 SBECD | 1:2.5 SBECD | 0.291 | 24/2 °C to 8 °C | 0.013 | 0.283 | 4.77 |
| 1:2.2 SBECD | 1:2.5 SBECD | 0.112 | 24/2 °C to 8 °C | 0.005 | 0.106 | 4.73 |
| 1:1.1 SBECD | 1:1.4 SBECD | 0.291 | 16/RT | 0.024 | 0.289 | 8.55 |
| 1:1.1 SBECD | 1:1.4 SBECD | 0.112 | 16/RT | 0.009 | 0.109 | 8.07 |
| 1:2.2 HPBCD | 1:2.6 HPBCD | 0.291 | 16/RT | 0.023 | 0.292 | 8.13 |
| 1:2.2 HPBCD | 1:2.6 HPBCD | 0.112 | 16/RT | 0.008 | 0.109 | 7.80 |
| 1:1.1 SBECD:1.1 HPBCD | 1:2.5 CD (SBECD + HPBCD) | 0.291 | 16/RT | 0.021 | 0.294 | 7.32 |
| 1:1.1 SBECD:1.1 HPBCD | 1:2.5 CD (SBECD + HPBCD) | 0.112 | 16/RT | 0.008 | 0.110 | 7.11 |

*The finished product molar ratio is calculated from HPLC assay results of the lyo cakes.

Example 10. Long-Term Aqueous Stability of the CBT Succinate-CD Inclusion Complexes at 2 °C to 8 °C To evaluate aqueous stability of the CBT succinate-CD inclusion complexes, the crude CBT succinate-CD inclusion complexes obtained by the ball milling process described in Example 7 were dissolved by 20 mM pH 8.0 phosphate buffer, then filtered through 0.22 μm syringe filters. The resulting aqueous samples were kept at 2 °C to 8 °C for a predetermined time for stability monitoring. After that, HPLC as described in Example 5 was used to determine the CBT succinate concentrations. The results are tabulated in Table 7 as below.

Another aqueous stability study was further carried out with the 1:2.2 SBECD formulation. Similarly, the crude CBT succinate-SBECD inclusion complexes were obtained by the ball milling process described in Example 7, dissolved by 35 mM pH 7.5 phosphate buffer, then filtered through 0.22 μm syringe filters. A portion of the resulting aqueous samples were kept at 2 °C to 8 °C for a predetermined time for stability monitoring. After that, HPLC assay as described in Example 5 was used to determine CBT succinate concentrations. The results are tabulated in Table 8 as below.

TABLE 8

Long-term aqueous stability of the 1:2.2 SBECD formulation at 2 °C to 8 °C

| | Day 0 conc. (mg/g) | 2 Months conc. (mg/g) | 3 Months conc. (mg/g) | 4 Months conc. (mg/g) |
|---|---|---|---|---|
| 1:2.2 SBECD | 10.45 | 10.32 | 10.34 | 9.75 |

Generally, the reduction of 10% can be a standard for determining whether a drug expires or not. The aqueous stability demonstrated a satisfactory in-use stability for 3 months. This is a significant improvement from the commercial product, Jevtana Kit requiring two-step dilutions due to poor aqueous stability, where per its labeling:

"The second dilution should be done immediately (within 30 minutes) to obtain the final infusion. The final infusion should be used within 8 hours at ambient temperature (including the one-hour infusion) or within a total of 24 hours if refrigerated (including the one-hour infusion). As the final infusion solution is supersaturated, it may crystallize over time. Do not use if this occurs and discard."

Example 11. Long-Term Stability of the CBT Succinate-CD Inclusion Complexes as Lyo-Cake at 2 °C to 8 °C Another portion of the resulting aqueous sample which was used in Table 8 of Example 10 was further lyophilized and stored as a lyo cake at 2 °C to 8 °C for a predetermined time for long term stability analysis. At designated time points, the CBT succinate content in the lyo cake was determined by HPLC assay as described in Example 5 and expressed as weight % of the lyo cake. The results are tabulated in Table 9 as below. The inclusion complex product remained very stable.

TABLE 9

Long-term stability of the 1:2.2 SBECD inclusion complex lyo cake at 2 °C to 8 °C

| | Initial weight % of CBT Succinate in the lyo cake | 1 Month weight % of CBT Succinate in the lyo cake | 3 Months weight % of CBT Succinate in the lyo cake | 6 Months weight % of CBT Succinate in the lyo cake |
|---|---|---|---|---|
| 1:2.2 SBECD | 14.66 | 14.89 | 15.19 | 14.69 |

Example 12. In Vivo PK Bioconversion (IV Bolus) of CBT Succinate-HPBCD in Mice To evaluate whether CBT succinate administered as CBT succinate-HPBCD inclusion complex could be quickly released and hydrolyzed to the CBT (parent drug) after IV injection, CBT succinate and HPBCD (1:4) were mixed and the CBT succinate-HPBCD inclusion complex was prepared by method described in Example 6 and purified by dissolving in water and filtering with a 0.45 μm filter. After that, the CBT succinate-HPBCD inclusion complex lyo cake was reconstituted with normal saline to 5.9 mg/mL and dosing at 16.8 mg/kg in mice (IV bolus, the CBT succinate-HPBCD inclusion complex was quickly injected into the vein). Plasma concentrations of CBT and CBT succinate were analyzed by LC-MS/MS. Animal test was carried out as described in Example 4, except injecting said CBT succinate-HPBCD inclusion complex (16.8 mg/kg, IV). The bioanalysis results are tabulated as Tables 10 to 12 below.

TABLE 10

The exposure levels of CBT succinate in mouse plasma samples - CBT succinate-HPBCD inclusion complex (16.8 mg/kg, IV) group:

| Time (h) | CBT Succinate concentration (ng/mL) | | | Mean | SD |
|---|---|---|---|---|---|
| 0.083 | 15550 | 17380 | 13198 | 15376 | 2096 |
| 0.167 | 4491 | 3982 | 4239 | 4237 | 255 |
| 0.5 | 341 | 392 | 370 | 368 | 26 |
| 1 | 18 | 35 | 33 | 29 | 9 |
| 2 | 27 | 16 | 21 | 21 | 6 |
| 4 | BLOQ | BLOQ | BLOQ | BLOQ | N/A |
| 8 | BLOQ | BLOQ | BLOQ | BLOQ | N/A |
| 24 | BLOQ | BLOQ | BLOQ | BLOQ | N/A |

TABLE 11

The exposure levels of Cabazitaxel in mouse plasma samples - CBT succinate-HPBCD inclusion complex (16.8 mg/kg, IV) group:

| Time (h) | CBT concentration (ng/mL) | | | Mean | SD |
|---|---|---|---|---|---|
| 0.083 | 12627 | 14778 | 11575 | 12993 | 1633 |
| 0.167 | 4298 | 4042 | 3951 | 4097 | 180 |
| 0.5 | 410 | 418 | 358 | 395 | 33 |
| 1 | 29 | 52 | 39 | 40 | 12 |
| 2 | 36 | 35 | 37 | 36 | 1 |
| 4 | BLOQ | 19 | BLOQ | 19 | N/A |
| 8 | BLOQ | BLOQ | BLOQ | BLOQ | N/A |
| 24 | BLOQ | BLOQ | BLOQ | BLOQ | N/A |

TABLE 12

The PK parameters of CBT succinate and CBT in mouse plasma samples - CBT succinate-HPBCD inclusion complex (16.8 mg/kg, IV):

| CBT Succinate 16.8 mg/kg, IV | | CBT Succinate | CBT |
|---|---|---|---|
| $t_{1/2}$ | (h) | 0.21 | 2.68 |
| $C_0$ | (ng/mL) | 54950 | 40643 |
| AUClast | (h*ng/mL) | 4633 | 3893 |
| AUCInf | (h*ng/mL) | 4640 | 3967 |
| AUC/D | (h*kg*ng/mL/mg) | 276 | 264 |
| AUC Extr | (%) | 0.14 | 1.85 |
| MRT | (h) | 0.08 | 0.28 |
| Vss | (L/kg) | 0.30 | 1.06 |
| CL | (mL/min/kg) | 60.35 | 63.02 |

The results demonstrated that the bioconversion of CBT succinate to CBT happened quickly in mice when a CBT succinate-HPBCD inclusion complex was used for administration. Compared with the preclinical formulation (50% PEG300 in normal saline) data in Example 4 and Tables 1-3, there could be a slight delay in the bioconversion due to HPBCD complexation effect. As suggested by the larger AUC of CBT succinate than that of CBT in the CBT succinate-HPBCD inclusion complex study, it shows that the CBT succinate-CD inclusion complex is the other way around in the preclinical formulation (50% PEG300 in normal saline) study.

Example 13. In Vivo PK Bioconversion (1 h Infusion) of CBT Succinate-SBECD in Mice To simulate clinical 1 hour IV infusion dosing regimen of Jevtana Kit, a CBT succinate-SBECD inclusion complex lyo cake was obtained by methods described in Example 11

(with a starting materials CBT succinate and SBECD molar ratio of 1:2.2 and a finished product CBT succinate and SBECD molar ratio=1:2.48) were reconstituted with normal saline to 2.8 mg/mL then perform 1 hour IV infusion at 16.8 mg/kg in mice.

A pharmacokinetic (PK) study was performed in male ICR mice (30±5 g) following intravenous continuous infusion (IV-CI) of Cabazitaxel succinate-SBECD inclusion complex at 16.8 mg/kg, over a one-hour (1 h) duration through swivel system. The plasma samples were collected at 0.083, 0.167, 0.5, 1, 2, 4, 8, and 24 h after infusion. Few days before administration, the mice were anesthetized with pentobarbital at 80 mg/kg through intraperitoneal (IP) injection. A PU-25 catheter was inserted into both right JV and left CA, tunneled subcutaneously to the dorsal incision, exteriorized in the scapular region and secured. The analgesic agent [meloxicam (20 mg/kg, QD×1, SC injection); all groups] was given prior to the surgery to prevent the post-surgical pain. The right JV was applied for the test article infusion and the left CA was used for the blood withdrawn. Continuous IV infusion (1 h duration) was performed through the right JV, by using swivel system and syringe pump in conscious and freely moving mice. Since some blood collection time points were close, the mice were grouped into two (three mice for each group) and blood collection was carried out alternately by the two groups. Blood aliquots were collected from the mice via CA catheter (~100 μL) for the first three time points or cardiac puncture (~300 μL) for the last time point from mice in tubes coated with lithium heparin, mixed gently, and centrifuged at 2,500×g for 15 minutes at 4 °C, within 1 hour of collection. The plasma samples were then harvested and kept frozen at ≤−70 °C until further processing.

Plasma concentrations of CBT and CBT succinate were analyzed by LC MS/MS. Animal test was carried out as described in accordance with Example 4, except injecting said CBT succinate-SBECD inclusion complex (16.8 mg/kg, IV). The bioanalysis results are tabulated as Tables 13 to 14 below:

TABLE 13

The exposure levels of CBT succinate in mouse plasma samples - CBT succinate-SBECD inclusion complex (16.8 mg/kg, 1 h infusion) group:

| Time (h) | CBT Succinate concentration (ng/mL) | | | Mean | SD |
|---|---|---|---|---|---|
| 0.083 | 344 | 366 | 183 | 298 | 100 |
| 0.167 | 133 | 141 | 212 | 162 | 43 |
| 0.5 | 32 | 17 | 16 | 22 | 9 |
| 1 | BLOQ | BLOQ | 5 | 5 | N/A |
| 2 | BLOQ | BLOQ | 5 | 5 | N/A |
| 4 | BLOQ | BLOQ | BLOQ | BLOQ | N/A |
| 8 | BLOQ | BLOQ | BLOQ | BLOQ | N/A |
| 24 | BLOQ | BLOQ | BLOQ | BLOQ | N/A |

TABLE 14

The exposure levels of Cabazitaxel in mouse plasma samples - CBT succinate-SBECD inclusion complex (16.8 mg/kg, 1 h infusion) group:

| Time (h) | CBT concentration (ng/mL) | | | Mean | SD |
|---|---|---|---|---|---|
| 0.083 | 381 | 354 | 197 | 311 | 99 |
| 0.167 | 145 | 145 | 204 | 165 | 34 |
| 0.5 | 29 | 21 | 20 | 23 | 5 |
| 1 | 8 | 7 | 6 | 7 | 1 |
| 2 | 5 | 6 | BLOQ | 6 | 1 |

TABLE 14-continued

The exposure levels of Cabazitaxel in mouse plasma samples - CBT succinate-SBECD inclusion complex (16.8 mg/kg, 1 h infusion) group:

| Time (h) | CBT concentration (ng/mL) | | | Mean | SD |
|---|---|---|---|---|---|
| 4 | 6 | BLOQ | 7 | 7 | 1 |
| 8 | BLOQ | BLOQ | BLOQ | BLOQ | N/A |
| 24 | BLOQ | BLOQ | BLOQ | BLOQ | N/A |

Due to plasma concentrations during the 1 hour infusion period were not determined in this PK study, a majority portion of the AUC was not captured thus several PK parameters were not calculable. However, it was still demonstrated that the bioconversion of CBT succinate to CBT took place as predicted when a CBT succinate-SBECD inclusion complex was used for administration.

From above, it can be found that the pharmaceutical composition of the present invention has an improved aqueous solubility and long-term storage stability, and can be effectively converted into CBT in vivo. The pharmaceutical composition comprises no polysorbate 80 (surfactant, which may result in diarrhea and hypersensitivity reactions in patients) or alcohol (which may result in intoxication), and allows administration of cabazitaxel to patients without the need of premedication.

What is claimed is:

1. A pharmaceutical composition comprising a cabazitaxel prodrug-cyclodextrin inclusion complex, which comprises: (a) a cabazitaxel prodrug represented by Formula 1 or a pharmaceutical acceptable salt thereof, and (b) a cyclodextrin (Formula 1)

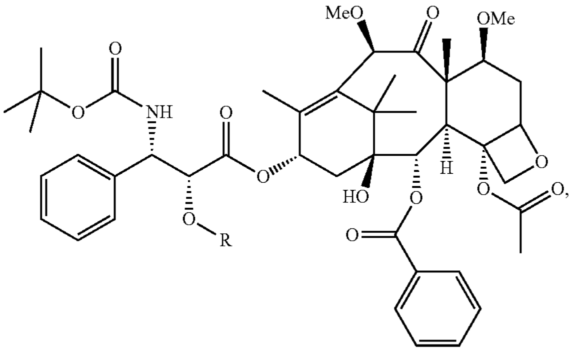

wherein, R—O— is $R^1$—C(═O)—O—, $C_6H_5C(═O)$—O— or $(NO_2)$—$C_6H_4C(═O)$—O—; and $R^1$ is a non-substituted straight alkyl carboxylic acid group having a total number of 1 to 30 carbons.

2. The pharmaceutical composition of claim 1, wherein the cabazitaxel prodrug is cabazitaxel oxalate, cabazitaxel malonate, cabazitaxel succinate, cabazitaxel glutarate, cabazitaxel adipate, cabazitaxel pimelicate, cabazitaxel subericate, cabazitaxel azelaicate, cabazitaxel sebacicate, cabazitaxel undecanedioic acid ester, cabazitaxel dodecanedioic acid ester, cabazitaxel tridecanedioic acid ester, cabazitaxel hexadecanedioic acid ester, cabazitaxel heneicosanedioic acid ester, cabazitaxel docosanedioic acid ester, cabazitaxel triacontanedioic acid ester, cabazitaxel maleicate, cabazitaxel fumarate, cabazitaxel glutaconate, cabazitaxel (e)-pent-2-enedioic acid ester, cabazitaxel 2-decenedioic acid ester, cabazitaxel traumatate, cabazitaxel muconate, cabazitaxel glutinate, cabazitaxel citraconate, cabazitaxel mesaconate, cabazitaxel itaconate, or cabazitaxel acetylenedicarboxylate.

3. The pharmaceutical composition of claim 1, wherein the cabazitaxel prodrug is cabazitaxel benzoate or cabazitaxel nitrobenzoate.

4. The pharmaceutical composition of claim 1, wherein the cyclodextrin is selected from α-cyclodextrin, β-cyclodextrin, γ-cyclodextrin, or a combination thereof.

5. The pharmaceutical composition of claim 1, wherein said cabazitaxel prodrug and cyclodextrin are in a molar ratio of cabazitaxel prodrug to cyclodextrin from about 1:30 to about 1:0.5.

6. The pharmaceutical composition of claim 1, wherein said cabazitaxel prodrug and cyclodextrin are in a molar ratio of cabazitaxel prodrug to cyclodextrin from about 1:30 to about 1:1.

7. The pharmaceutical composition of claim 1, wherein said cabazitaxel prodrug and cyclodextrin are in a molar ratio of cabazitaxel prodrug to cyclodextrin from about 1:30 to about 1:2.

8. The pharmaceutical composition of claim 1, wherein said pharmaceutical composition is in a form selected from aqueous solution, lyophilized powder and oral dosage forms.

9. The pharmaceutical composition of claim 1, which further comprises at least one pharmaceutically acceptable excipient.

10. The pharmaceutical composition of claim 1, which is free of polysorbate 80.

11. A method of treating a tumor in a subject in need thereof, comprising administering to the subject a therapeutically effective amount of the pharmaceutical composition of claim 1.

* * * * *